US008703849B2

(12) United States Patent
Hagberg et al.

(10) Patent No.: US 8,703,849 B2
(45) Date of Patent: Apr. 22, 2014

(54) PROCESSES FOR MAKING HIGH PURITY RENEWABLE SOURCE-BASED PLASTICIZERS AND PRODUCTS MADE THEREFROM

(75) Inventors: Erik Hagberg, Decatur, IL (US); Stephen Howard, Sherman, IL (US); George Poppe, Forsyth (IL); Stephen D. Horton, Avon Lake, OH (US)

(73) Assignee: Archer Daniels Midland Company, Decatur, IL (US)

( * ) Notice: Subject to any disclaimer, the term of this patent is extended or adjusted under 35 U.S.C. 154(b) by 2 days.

(21) Appl. No.: 13/519,956

(22) PCT Filed: Jan. 4, 2011

(86) PCT No.: PCT/US2011/020095
§ 371 (c)(1),
(2), (4) Date: Jun. 29, 2012

(87) PCT Pub. No.: WO2011/090812
PCT Pub. Date: Jul. 28, 2011

(65) Prior Publication Data
US 2012/0277357 A1   Nov. 1, 2012

Related U.S. Application Data

(60) Provisional application No. 61/297,317, filed on Jan. 22, 2010.

(51) Int. Cl.
*C08K 5/1515* (2006.01)
*C11C 1/06* (2006.01)
*C07D 301/02* (2006.01)
*C07D 301/00* (2006.01)
*C08L 27/06* (2006.01)
*C11C 3/10* (2006.01)

(52) U.S. Cl.
USPC ........... 524/114; 524/569; 106/504; 554/167; 554/171; 549/513; 549/518

(58) Field of Classification Search
CPC .... C08K 5/0016; C08K 5/1515; C08L 27/06; C07C 69/66; C07C 69/52; C08G 59/145; C11C 3/003
USPC ........... 524/114, 569; 106/504; 554/167, 171; 549/513, 518
See application file for complete search history.

(56) References Cited

U.S. PATENT DOCUMENTS

| 3,377,301 A | 4/1968 | Kuester et al. |
| 3,377,304 A * | 4/1968 | Kuester et al. ............ 524/114 |
| 2009/0149585 A1 | 6/2009 | DeQuadros et al. |
| 2009/0149586 A1 | 6/2009 | DeQuadros et al. |

FOREIGN PATENT DOCUMENTS

| GB | 815301 | 6/1959 |
| GB | 1049100 | * 11/1966 |

OTHER PUBLICATIONS

Witnauer et al. (J. Indust. Engg. Chem., v47, n11, 1955, p. 2304-2311)—"Epoxy Esters as Plasticizers and Stabilizers for Vinyl Chloride Polymers".*
Specialty Plasticisers (The Plasticisers and Flexible PVC Information Centre, European Council for Plasticisers and Intermediates—2010—http://www.plasticisers.org/plasticisers/specialty-plasticisers#Secondary Plasticisers).*
WO2011-090812A2—International Search Report—Jan. 29, 2013.*
Witnauer et al., "Epoxy Esters as Plasticizers and Stabilizers for Vinyl Chloride Polymers", (J. Indust. Engg. Chem., v47, n11, 1955, p. 2304-2311).*
Gan et al., Epoxidized Esters of Palm Olein as Plasticizers for Poly(Vinyl Chloride), Eur. Polym. Journal. vol. 31, No. 8, pp. 719-724, 1995, Great Britain.
Norris et al., Fatty Acid Esters of Furfuryl Alcohol, Oil & Soap, Jul. 1944, pp. 193-196.
Lewis et al., Epoxide plasticizer-stabilizer for poly(vinyl chloride) from -campholenol, A terpene-derived primary alcohol, I & EC Product Research and Development, vol. 4 No. 4, pp. 231-233, Dec. 1965.
Frankel et al., Acyl Esters from Oxo-Derived Hydroxymethylstearates as Plasticizers for Polyvinyl Chloride, Journal of the American Oil Chemists' Society, vol. 52 pp. 498-504, Dec. 1975.
Howell et al., Benzyl bis-(Epoxy)linoleate as a Model for Expoxidized Soybean Oil, Center for Applications in Polymer Science and Department of Chemistry, Polymeric Materials Science and Engineering, 1991, pp. 167-168.

* cited by examiner

Primary Examiner — Ling Choi
Assistant Examiner — Ronald Grinsted
(74) Attorney, Agent, or Firm — William B. Miller

(57) ABSTRACT

Presently disclosed are high purity unsaturated fatty acid esters with an ester moiety characterized by having from five to seven members in a ring structure, which esters when epoxidized find particular utility as primary plasticizers in flexible polyvinyl halide applications. Also disclosed are processes for making the high purity esters.

12 Claims, 4 Drawing Sheets

Figure 1:
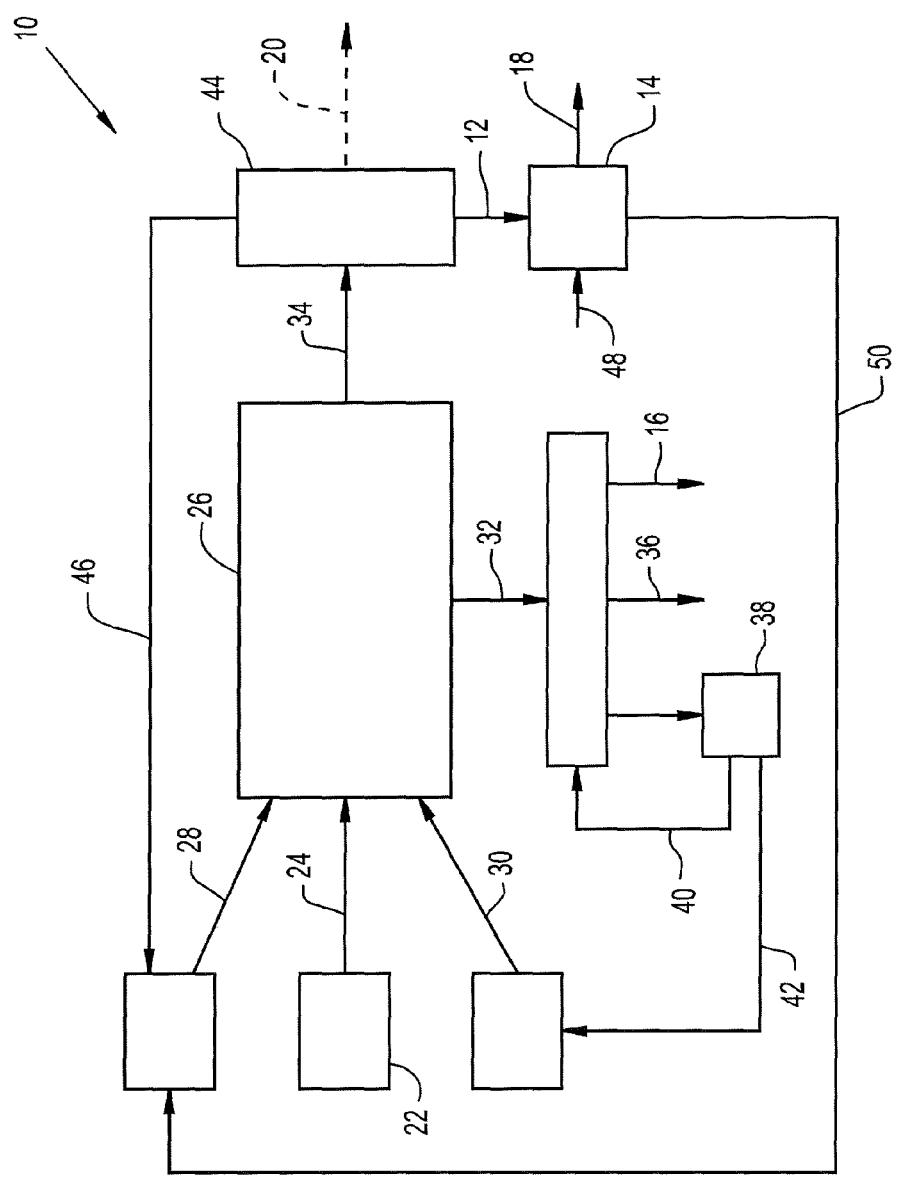

PROCESSES FOR MAKING HIGH PURITY RENEWABLE SOURCE-BASED PLASTICIZERS AND PRODUCTS MADE THEREFROM

This invention relates to polyvinyl halide plasticizers which have been derived from renewable materials, such as vegetable oil, to the methods by which such plasticizers are made and to the polyvinyl halide compositions incorporating these plasticizers.

Polyvinyl chloride (PVC), the most common vinyl halide polymer, finds commercial application in a rigid, substantially unplasticized form and in a plasticized PVC form.

Rigid PVC, with which the present invention is not concerned, is used for pipework, ducts and the like in which high chemical resistance is needed but not flexibility or pliability. Plasticized PVC, on the other hand, finds application in films, sheeting, wire and cable coverings, moldings, conveyor belting, toys and hose, in addition to serving as a leather substitute and as a fabric covering for upholstered furniture, automotive seating and other articles.

Broadly speaking, plasticizers are materials which are combined with polymers such as polyvinyl chloride (hereinafter, PVC) to impart flexibility, extensibility and workability or some combination of these attributes to the polymer, as needed for a particular end use. Frequently, a combination of primary and secondary plasticizers is used, with the secondary plasticizers not acting in and of themselves to impart the desired attributes to the PVC but serving to improve the effectiveness of the primary plasticizer(s) and optionally offering other characteristics to a PVC composition in which the materials are incorporated.

Historically, the majority of primary PVC plasticizers have been petroleum-derived phthalates and benzoate compounds, dioctyl phthalate and diisononyl phthalate being notable examples. However, such petroleum-derived plasticizers are frequently expensive to produce and use because of fluctuations in the pricing and availability of petroleum, and are increasingly likely to remain so as petroleum reserves are reduced and new supplies prove more costly and difficult to secure. Further, certain of the petroleum-derived phthalate plasticizers have raised concerns for their potential to disrupt human endocrine activity, and regulatory controls have been established in a number of countries to address these concerns.

Unmodified vegetable oils are largely incompatible with PVC resin, but certain modified derivatives of vegetable oils, such as epoxidized soybean oil (ESO), are compatible with PVC resin and have been actively investigated for use as a lower cost, renewable source-based alternative to the petroleum-based plasticizers, both as primary and secondary plasticizers. The interest in developing useful plasticizers from renewable sources, such as vegetable oils, has developed partly also from the expectation that such materials would be less likely to cause physiological disturbances or other injuries to persons coming into contact with products which require plasticizers in their composition.

As related in U.S. Pat. No. 6,797,753 to Benecke et al., however, these modified vegetable oil derivatives have been used to a limited extent commercially as secondary plasticizers only, because of compatibility limitations in PVC. Benecke et al. and others have accordingly sought to identify further modifications or other vegetable oil-derived materials with improved compatibility for use as a primary plasticizer, while retaining the beneficial thermal stabilization properties of epoxidized soybean oil. Notwithstanding these efforts, plasticizers based on vegetable oils have up until the present invention not proven to be a commercially viable, renewable source-based, primary plasticizer alternative to the phthalate and phthalate ester petroleum-based primary plasticizers.

In a first aspect, the present invention concerns processes for making high purity unsaturated fatty acid esters with an ester moiety characterized by having from 5 to 7 members in a ring structure, whether cyclic, heterocyclic or aromatic in character. Epoxidized versions of these esters can (according to a second aspect) be used as renewable source-based plasticizers for polyvinyl halide polymers, and in particular, for PVC. The plasticizers enabled by the present invention can be incorporated easily into PVC as primary plasticizers at even plastisol levels, and provide plasticized PVC compositions in turn that have improved and unexpected characteristics.

Parenthetically, "PVC" or "polyvinyl chloride" as used herein will be understood to cover the range of homo- and copolymer resins of vinyl chloride in which the inventive plasticizers may find use, especially as a primary plasticizer. Similarly, "polyvinyl halide" will be understood as embracing both homo- and copolymer resins based on vinyl halides other than vinyl chloride. Exemplary copolymers of vinyl chloride include those containing up to about 20% of such monomers as vinyl acetate, propylene, ethylene, diethyl maleate, dimethyl fumarate, and other ethylenically unsaturated monomers).

While epoxidized benzyl esters of unsaturated fatty acids have been described or suggested previously for plasticizing PVC, see for example, U.S. Pat. No. 3,377,304 (epoxidized benzyl soyate) and GB 1,049,100, the known methods of making those benzyl esters and subsequent plasticizers result in PVC compositional limitations and performance characteristics which have unfortunately limited the use of such materials only to be secondary plasticizers and thermal stabilizers.

We have found that by preparing the indicated unsaturated fatty acid esters (including, of course, benzyl soyate esters) according to certain novel methods, these limitations on plasticizer usage can be overcome for the epoxidized versions of these esters, yielding materials which can be suitably used as primary plasticizers in polyvinyl halide compositions at unexpectedly high loadings and with improved—and in some cases, unexpected—properties in the resulting compositions.

FIG. 1 schematically illustrates a process for making an industrial grade or better glycerol product, an unsaturated fatty acid ester product according to the present invention and optionally a vegetable oil-derived biodiesel product, according to a preferred embodiment.

Figure 2:
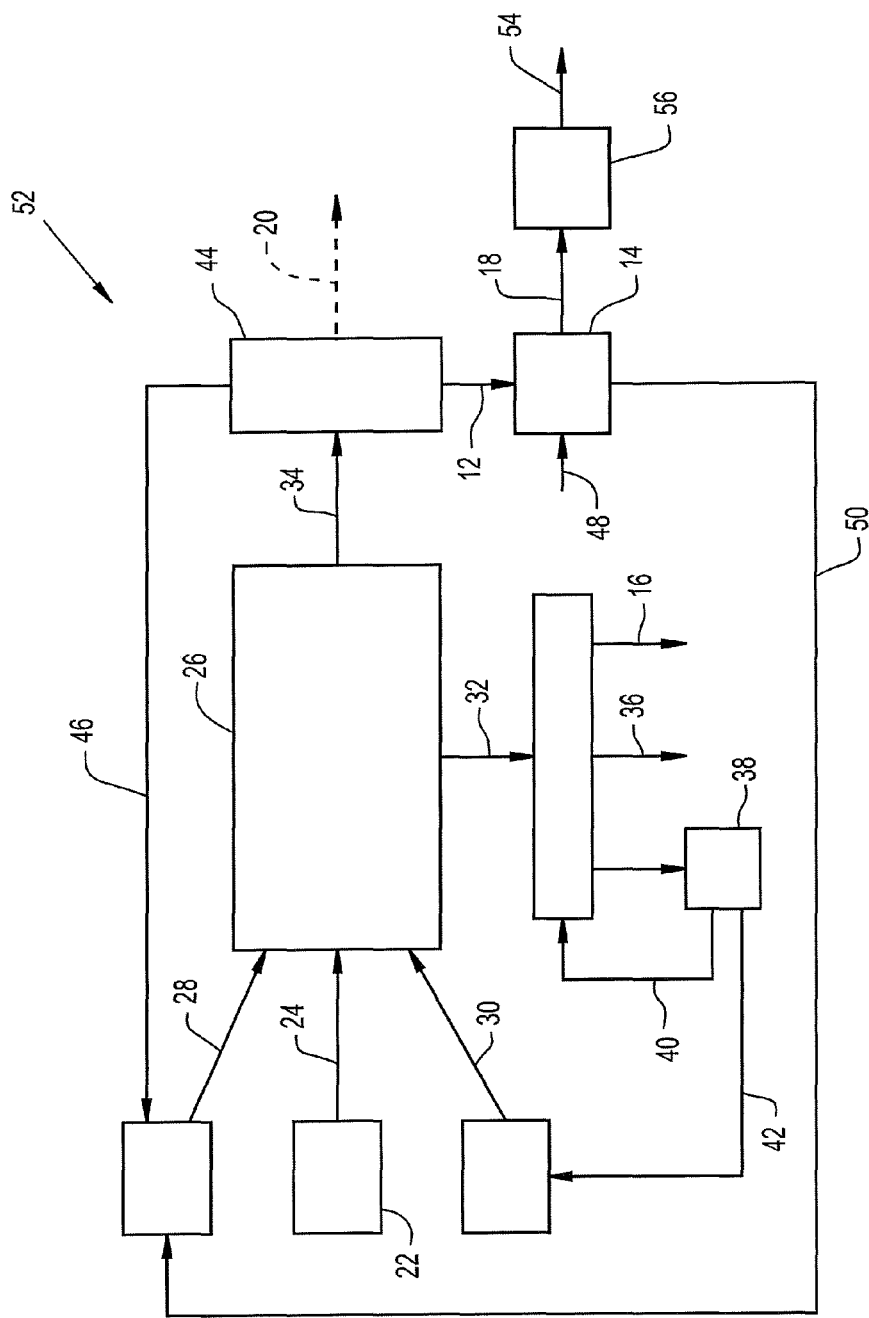

FIG. 2 schematically illustrates a process for making an industrial grade or better glycerol product, an epoxidized unsaturated fatty acid ester plasticizer product according to the present invention and optionally a vegetable oil-derived biodiesel product, according to a preferred embodiment.

Figure 3:
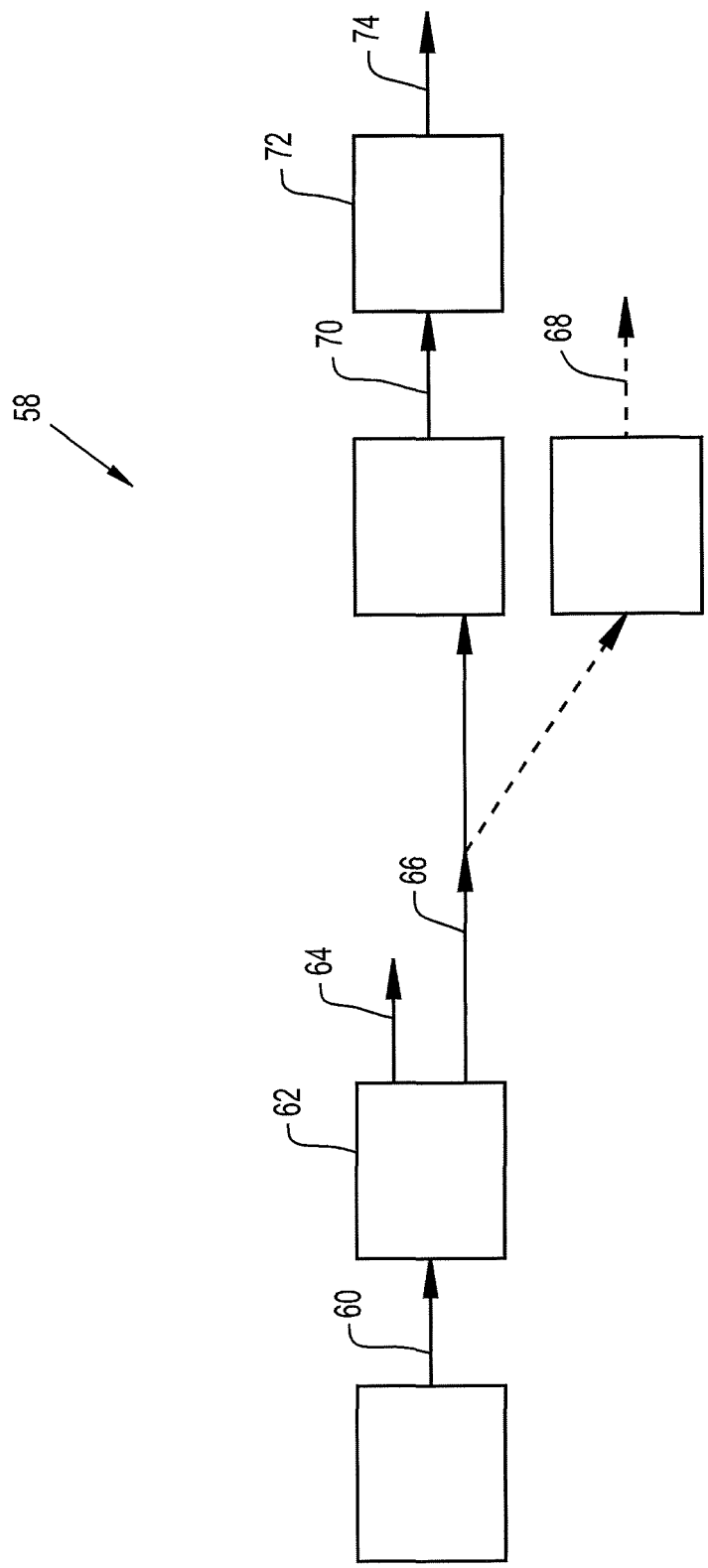

FIG. 3 schematically illustrates a process for making an epoxidized unsaturated fatty acid ester plasticizer product of the present invention, according to an alternate embodiment.

Figure 4:

FIG. 4 is a color photograph of specimens of PVC plastisols formulated as described in Examples 17 and 18 using epoxidized benzyl soyates according to the present invention and two commercial phthalate plasticizers, following heat stability testing.

The present invention is more readily understood in one aspect by reference to FIG. 1, in which an integrated process 10 is schematically illustrated for making an industrial grade or better glycerol product, an unsaturated fatty acid ester product as described above and optionally including a biodiesel product.

In the process 10, generally speaking, a process for the continuous production of lower alkyl esters of higher fatty acids for use as a biodiesel fuel (and many variants of such a process are known and have been practiced commercially) is modified to include the preparation of the unsaturated fatty acid ester product. The unsaturated fatty acid lower alkyl esters are thus used at least in part as a feedstock for the ester preparation, with a lower alkanol recycle loop being preferably included to recycle at least a portion of the lower alkanol originally used in the preparation of the unsaturated fatty acid lower alkyl esters.

In this regard, as is well-known, biodiesel fuels are presently made by the transesterification reaction of such lower alkanols with higher fatty acid triglycerides, to yield lower alkyl esters of higher fatty acids and a substantial glycerol co-product. The higher fatty acid triglycerides may derive from animal or vegetable (plant) sources, or from a combination of animal and vegetable sources as well known, and a variety of processes have been described or are known. The description of the present invention will refer primarily to vegetable oil-based biodiesel processes for simplicity's sake, but those skilled in the biodiesel art especially will appreciate that doing so should not be taken as so limiting the utility of the present invention.

In the context of vegetable oil-based biodiesel production, all sorts of vegetable oils have been combined with the lower aliphatic alcohols. Preferred vegetable oils include, but are not limited to, soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives, conjugated derivatives, genetically-modified derivatives and mixtures thereof. As used herein, a reference to a vegetable oil includes all its derivatives as outlined above. For instance, the use of the term "linseed oil" includes all derivatives including conjugated linseed oil.

The higher fatty acids which are especially of interest include fatty acids containing carbon chains of about 2 to about 24 carbons. More preferably, the carbon chain contains about 12 to about 24 carbons. Most preferably, the number of carbons is about 16 to about 18. Given that sites of unsaturation can be epoxidized by methods that are known in the art, and that the epoxidized fatty acid esters of those alcohols including a five to seven member ring structure have been found by the present invention to be particularly useful for plasticizing polyvinyl halide polymers, the fatty acids will preferably include one or more sites of unsaturation. A fatty acid that has a plurality of sites of unsaturation can be epoxidized to a greater extent, and so fatty acids having more than one site of unsaturation are generally preferred (together with the vegetable oils containing more of the fatty acids of this character, so that for example soybean oil is generally preferred to the more saturated palm oil as a starting material).

A number of homogeneous and heterogeneous catalysts are likewise known for catalyzing the formation of the lower alkyl esters from which the desired fatty acid esters or epoxidized esters will be made, for example, metal hydroxides, metal alkoxides, basic or acidic resins, metal hydrides, metal carbonates, metal acetates or various acids, especially with sodium alkoxide or hydroxide or potassium hydroxide. Both base and acid catalyzed processes have been described in the art, though the embodiment 10 is especially directed to base-catalyzed processes.

Exemplary references describing base-catalyzed processes for making the lower alkyl esters of higher fatty acids and an industrial grade or better glycerol co-product include U.S. Pat. No. 5,354,878 to Connemann et al. (the disclosure of which is hereby incorporated by reference), U.S. Pat. No. 5,399,731 to Wimmer, U.S. Pat. No. 5,424,466 to Stern et al., U.S. Pat. No. 5,849,939 to Mittelbach et al., U.S. Pat. No. 6,489,496 to Barnhorst et al. and U.S. Pat. No. 6,696,583 to Koncar et al.

We have fundamentally found in relation to the process 10 of the present invention, in which a base-catalyzed biodiesel process is modified to use at least a portion of the biodiesel as a feed for the preparation of unsaturated fatty acid esters (and/or epoxidized unsaturated fatty acid esters as described below) as well as the conventional industrial grade or better biobased glycerol co-product from these biodiesel processes, that when biodiesel fuel grade materials of a certain quality are used for preparing the benzyl esters and epoxidized benzyl esters, for example, which have been suggested for use as PVC plasticizers—but which have been heretofore found suitable only as secondary plasticizers or thermal stabilizers—the resultant benzyl esters and epoxidized benzyl esters behave very differently and unexpectedly much better in polyvinyl halide compositions as compared to those benzyl esters and epoxidized benzyl esters made in the aforementioned U.S. Pat. No. 3,377,304 to Kuester et al. and GB 1,049,100.

We have found, more particularly, that epoxidized fatty acid esters made by our processes can be incorporated and used in PVC as primary plasticizers, even at plastisol levels ranging upwards from 20 percent by weight, without unacceptably (or excessively) exuding from the resulting compositions.

Further, we have found that these epoxidized fatty acid esters have a high degree of permanence when used in such PVC compositions, exhibiting a lower than expected loss of mass in heat stability testing, despite the esters themselves having a relatively high intrinsic volatility.

A plasticized PVC composition's retention of other properties after aging, especially mechanical properties such as tensile strength and retention of elongation (retained elasticity, pliability and flexibility), is key to the commercial attractiveness of a proposed plasticizer for many end uses—and from this perspective we have demonstrated by the examples below that our epoxidized fatty acid esters provide plasticized PVC compositions with very desirable performance attributes. Thus, plasticized PVC compositions demonstrating a retention of elongation from an initial value corresponding to a non-heat treated sample, as elongation is determined according to ASTM D-638 (type 4), of at least about 50 percent, more preferably at least about 60 percent, and most preferably at least about 70 percent are enabled after heat treatment for one hour at 191° C.

The plasticized polyvinyl halide compositions of the present invention can be formulated, it is noted, in all other respects in a conventional manner, including various kinds of additives in addition to the inventive epoxidized esters as primary plasticizers. For example, a renewably-based secondary plasticizer and thermal stabilizer such as epoxidized soybean oil can be added, or other secondary plasticizers (including petroleum-based plasticizers) or other additives for improving one or more properties of heat stability, lubricity or weathering resistance, as ultraviolet absorbers, fillers, anti-oxidants, anti-static agents, anti-fogging agents, pigments, dyestuffs, crosslinking aids and the like can be incorporated in the compositions. The inventive epoxidized esters may also be blended with other primary plasticizers such as dioctylphthalate, other phthalates, citrates, benzoates, trimellitates, and other aliphatic diesters, though preferably the plasticized polyvinyl halide compositions of the present invention will not include any added phthalates and will include substantially only renewably-based or biobased plasticizers.

Turning back now to FIG. 1 in more detail, for the process 10 of making products including the inventive unsaturated fatty acid esters (which can then be epoxidized as schematically shown in FIG. 2 and used in the epoxidized form as primary plasticizers for polyvinyl halides), as has been previously mentioned, it is important for obtaining the performance attributes just listed to use a biodiesel fuel grade material 12 of a certain quality; namely, the material 12 fed to reactor 14 should contain not more than about 5.0 percent by weight combined of residual monoglycerides and diglycerides, preferably containing not more than about 2.0 percent, more preferably not more than about 0.4 percent and most preferably not more than about 0.25 percent by weight of monoglycerides and diglycerides.

Those familiar with the regulatory standards governing the manufacture and sale of unsaturated fatty acid alkyl esters in the United States and European markets, see, for example, ASTM D6751 and CEN 14214, will readily appreciate that biodiesel fuel grade materials meeting these standards should be suited for use as the feed 12 to the reactor 14 without need of any further purification or treatment, because the monoglyceride and diglyceride levels in compliant biodiesels under either the United States or European regulatory regimes will currently be well below 5.0 percent by weight of residual monoglycerides and diglycerides.

A preferably base-catalyzed transesterification process 10 for making an industrial grade or better glycerol product 16, an unsaturated fatty acid ester product 18 of the present invention and optionally a biodiesel product 20 (where not all of the unsaturated fatty acid lower alkyl esters, e.g., fatty acid methyl esters (FAMEs), are devoted to use as a feedstock for producing the unsaturated fatty acid ester product 18) can accordingly take a variety of forms and configurations, and so is described in but one preferred, general embodiment.

A source 22 of unsaturated higher fatty acid triglycerides, preferably being a vegetable oil such as soybean oil, provides a feed 24 to a transesterification reaction section 26, wherein the feed 24 is combined with a lower $C_1$-$C_5$ alcohol feed stream 28 (such as methanol) in the presence of an alkaline transesterification catalyst 30, for example, sodium methoxide, to undergo a transesterification reaction forming the corresponding lower alkyl esters of the fatty acids—in the case where methanol and soybean oil are used, $C_6$ to $C_{24}$ methyl soyate esters—along with co-product glycerol. The glycerol is separated (conventionally by settling) with residual catalyst and saponified fatty acids (conventionally by washing with a hot aqueous extraction solution) in stream 32, while the desired lower alkyl esters continue with unreacted alcohol in stream 34. The glycerol product 16 conventionally can be further purified, as desired, or used directly for other purposes (not shown).

As mentioned above, there are a variety of known processes, catalysts and apparatus for forming the lower alkyl fatty acid monoesters and co-product glycerol, but the particular details of these processes do not need to be reviewed here as they form no part of the present invention. The process as described in U.S. Pat. No. 5,354,878 to Connemann et al. can be used, with acidification of the saponified free fatty acids to yield the free fatty acids in a marketable product stream 36 and/or with adding an acid and base catalyst recovery step 38 as described in United States Published Application No. US 2009/0178928A1 to provide an acid stream 40 but also a recycle catalyst stream 42. Alternatively, a combined process to simultaneously both generate and separate out the lower alkyl monoesters and the co-product glycerol can be used, as described in United States Published Application No. US 2007/0158270A1, wherein simulated moving bed chromatography is employed. Still other variations are known or would be evident to those skilled in the art without undue experimentation for yielding at least the industrial grade or better glycerol product stream 16, the lower alkyl fatty acid monoesters in feed stream 12 and optionally forming a biodiesel product stream 20, but also possibly including the marketable free fatty acids 36 and enabling a separation and recycle of the alkaline transesterification catalyst as in stream 42 and of the acid in stream 40.

Stream 34 is then processed in a separation step 44 to separate the $C_1$-$C_5$ alcohol from the lower alkyl fatty acid monoesters desired to be used subsequently in feed stream 12 and optionally in a biodiesel product stream 20, for example, by means of a stripping column in which the alcohol is taken overhead, condensed and recycled in stream 46 to be used again in the alcohol feed 28.

Where a portion of the lower alkyl fatty acid monoesters are designated for the biodiesel product stream 20, some additional, conventional purification or processing can be employed by those skilled in the art, as needed to meet certain specifications for the stream 20. For example, biodiesel formed from soybean oil contains steryl glucoside contaminants which present difficulties for cold weather storage, distribution and use, and the art describes methods for removing steryl glucosides from the methyl soyate esters as illustrated by United States Published Patent Application Serial No. 2007/0151146A1.

For that portion of the lower alkyl fatty acid monoesters designated for use in feed stream 12 to the reactor 14, for making the inventive unsaturated fatty acid esters 18, optionally and preferably these lower alkyl fatty acid monoesters (e.g., methyl soyate esters) are subjected to procedures that cause enrichment on the basis of the degree of unsaturation of the esters. One such procedure, described in United States Published Patent Application No. 2007/0181504 (such application being hereby incorporated in the present application by reference), involves the use of argentation chromatography to produce a material that is highly enriched in unsaturated fatty acid esters. Another option would involve winterization (crystallization or fractionation) to produce a solid fraction enriched in the saturated fatty acid alkyl esters and a liquid fraction enriched in the unsaturated fatty acid alkyl esters.

Distillation of the lower alkyl fatty acid monoesters can also be used to produce a feed stream 12 which is enriched in the unsaturated fatty acid monoesters (as the bottoms from the distillation). Distillation is also conventionally used to generate biodiesels that are compliant with United States and European biodiesel regulatory standards as discussed above, and because the compliant biodiesels meet the requirements for the feed 12 in terms of monoacylglycerol/monoglyceride and diacylglycerol/diglyceride content, in general it will be preferred to simply use distillation of the crude biodiesel product 34 from reactor 26 in order to both meet the certain quality requirements of the feed 12 as well as provide a biodiesel fuel product 20 that meets United States and European regulatory standards—whether or not at a given time both feed 12 and biodiesel fuel stream 20 are being produced, or whether all of the unsaturated fatty acid alkyl esters are designated for use in feed stream 12. Distillation is also desirable for removing residual triglycerides, glycerol, steryl glucosides, water, alcohol and other nonfatty acid materials from the crude biodiesel stream 34.

Feed stream 12 thus generated, containing less than about 5.0 weight percent in total of monoglycerides and diglycerides and preferably less than about 2.0 percent by weight, more preferably less than about 0.4 percent by weight and most preferably less than about 0.25 percent by weight of such materials, is combined in reactor 14 with one or more preferably anhydrous alcohols 48 including from five to seven members in a ring structure, in the presence of an alkaline transesterification catalyst—which can be the same catalyst as used in the biodiesel preparation step in reactor 26, or a different catalyst—under conditions which are effective for forming the corresponding inventive esters from the unsaturated fatty acid monoesters in feed 12 along with preferably a second lower alkanol recycle stream 50, which recycles the lower alkanol used in the biodiesel preparation step back for reuse in that step. The reaction is conducted under reduced pressure with continual removal of the lower alkanol as the reaction proceeds to substantial completion. Excess alcohol (from the one or more alcohols 48) is removed after neutralization by washing and stripping steps.

Exemplary alcohols including five to seven membered ring structures include, but are not limited to, the following: benzyl alcohol (CAS 100-51-6); 2-chlorobenzenemethanol (CAS 17849-38-6); 3-chlorobenzenemethanol (CAS 873-63-2); 4-chlorobenzenemethanol (CAS 873-76-7); 2-bromobenzenemethanol (CAS 18982-54-2); 3-bromobenzenemethanol (CAS 15852-73-0); 4-bromobenzenemethanol (CAS 873-75-6); 2-methoxybenzenemethanol (CAS 612-16-8); 3-methoxybenzenemethanol (CAS 6971-51-3); 4-methoxybenzenemethanol (CAS 105-13-5); 2-furanmethanol (CAS 98-00-0); 3-furanmethanol (CAS 143632-21-7); 5-methyl-2-furanmethanol (CAS 3857-25-8); tetrahydro-2-furanmethanol (CAS 97-99-4); tetrahydro-3-furanmethanol (CAS 15833-61-1); tetrahydro-5-(methoxymethyl)furfuryl alcohol (CAS 872303-99-6); tetrahydro-sH-pyran-2-ol (CAS 694-54-2); tetrahydro-2H-pyran-3-ol (CAS 19752-84-2); tetrahydro-2H-pyran-4-ol (CAS 2081-44-9); tetrahydro-2H-pyran-2-methanol (CAS 100-72-1); tetrahydro-2H-pyran-3-methanol (CAS 14774-36-8); tetrahydro-2H-pyran-4-methanol (CAS 14774-37-9); 1,4:3,6-dianhydro-2-O-methylhexitol (CAS 1175065-15-2) and 1,4:3,6-dianhydro-2-deoxyhexitol (CAS 1078712-23-8).

Additional decolorizing treatments can be performed on the resulting inventive esters as desired, for example, by treatment of the product 18 with carbon or with some other suitable adsorbent.

Alternatively, the lower alkyl fatty acid esters can be treated initially by exposure to a borohydride to reduce peroxide and para-anisidine values of the ester feed 12 in the manner of commonly-assigned U.S. Pat. No. 7,126,018 to Poppe, prior to the transesterification of the lower alkyl esters to the inventive esters. As demonstrated by an example below, the resulting product esters 18 as well as the epoxidized esters prepared therefrom are characterized by a desirable very light yellow color.

In one preferred embodiment of the process 10, a feed stream 12 consisting essentially entirely of soy methyl esters, and from which residual moisture has been removed by drying with the application of heat and reduced pressure, is combined with anhydrous benzyl alcohol in the presence of an alkaline transesterification catalyst. The alkaline transesterification catalyst can be a sodium methoxide, potassium tert-butoxide or N-heterocyclic carbene catalyst.

A potassium tert-butoxide catalyst is presently preferred, because the sodium methoxide catalyst sets up an equilibrium with the methyl esters so that some methyl esters remain unconverted to the corresponding benzyl esters, whereas the potassium tert-butoxide catalyst is sterically hindered from establishing a similar equilibrium. Over time, as well, the sodium methoxide catalyst will have required fresh additions of catalyst to reach full conversion or substantially full conversion.

An example of a commercially available, suitably stable N-carbene catalyst (under air-free conditions) is 1,3-Bis(2,6-diisopropylphenyl)imidazol-2-ylidene (CAS 244187-81-3), from Sigma-Aldrich Co., though other N-carbene catalysts and preparation methods will be within the capabilities of those skilled in the art without undue experimentation.

The reaction is preferably carried out in the presence of the selected catalyst under reduced pressure, with neat reactants insofar as possible and in the absence of moisture, with continuous and preferably complete removal of the lower alkyl alcohol, and with agitation to help the reaction to at least substantial completion. The extent of reaction can preferably be measured by taking periodic samples and analyzing for how much of the methyl esters remain.

For the formation of the benzyl soyate esters in the presence of a sodium methoxide catalyst, "substantial completion" corresponds to a remaining methyl esters content of 2% by weight or less, while for the potassium tert-butoxide and N-heterocyclic carbene catalysts preferably less than about 2 mole percent of the methyl esters will remain.

Turning now to FIG. 2, a process 52 is schematically illustrated for making an industrial grade or better glycerol product 16, an epoxidized unsaturated fatty acid ester plasticizer product 54 according to the present disclosure and optionally a vegetable oil-derived biodiesel product 20, according to a preferred embodiment. The process 52 of FIG. 2, it will be seen, adds an epoxidation step performed on the unsaturated fatty acid ester product stream 18, to provide in an integrated process the plasticizers that we have found surprisingly useful as primary plasticizers for making plasticized (flexible) polyvinyl halide compositions, as described above.

Ester product stream 18 from process 10 is preferably continuously produced and then epoxidized in a reactor 56 using any conventional method for accomplishing the epoxidation, for example, by exposure of the esters in stream 18 to strongly acidic media, for example, a peracid supplied from an external source or generated in situ from hydroperoxides and an organic acid in a strong mineral acid solution, or through exposure to acidic solids in the presence of a catalyst. Exemplary epoxidation methods are described in, for example, commonly-assigned United States Published Application No. 2009/0005508 (which is incorporated herein by reference), U.S. Pat. Nos. 4,647,678, 6,740,763 and US Published Application No. 2008/0154053.

In a related alternative to the process 52, as exemplified below, the epoxidation step may be first carried out on the lower alkyl fatty acid esters (for example, soy methyl esters) in stream 12, and the transesterification step in reactor 14 thus carried out on epoxidized lower alkyl fatty acid esters rather than on the unepoxidized lower alkyl fatty acid esters. In a second related alternative, also exemplified below, instead of an alcohol including a five to seven membered ring structure, a corresponding ester can be used in stream 48 (benzyl acetate rather than benzyl alcohol, for example) and an interesterification carried out in the reactor 14 on the epoxidized lower alkyl fatty acid esters in stream 12. Of course, it will be appreciated in passing that the same five to seven membered ring esters may be used in the embodiment 10 of FIG. 1 or with the esterify first/epoxidize second mode of process 52 as shown in FIG. 2.

According to either of these two related alternatives to the process 52, in addition to an industrial grade glycerol product 16, marketable free fatty acids in stream 36, an optional biodiesel product 20 and the inventive epoxidized high purity unsaturated fatty acid ester primary plasticizer product 54, an epoxidized lower alkyl fatty acid ester product may also be obtained by withdrawing a portion of the epoxidized lower alkyl fatty acid esters before they undergo transesterification or interesterification as just described in the reactor 14. In this regard, epoxidized methyl soyate plasticizers have been previously known, so that in these two related alternatives to the process 52 both epoxidized methyl and epoxidized benzyl soyate plasticizer products may be made, for example.

FIG. 3 schematically depicts an alternative method for producing an industrial grade or better glycerol product, an epoxidized unsaturated fatty acid ester plasticizer product of the present invention and optionally a biodiesel product in the form of fatty acid lower alkyl esters. In the process 58, unsaturated higher fatty acid triglycerides present in animal and/or vegetable-based fats and oils 60 are chemically or enzymatically hydrolyzed according to well-known processes in a fat-splitting step 62 (for example, by a batch autoclave or continuous countercurrent, high pressure process) and then separated into an industrial grade or better glycerol product stream 64 and a free fatty acids feed stream 66.

The free fatty acids stream 66 should, we have found, have the same low residual monoacylglyceride (MAG) and diacylglyceride (DAG) contents indicated as appropriate for the fatty acid lower alkyl ester feed stream 12 in the process depicted in FIG. 1.

These levels are preferably achieved in the free fatty acids feed stream 66 by adjusting the hydrolysis conditions so that the fatty acid groups are substantially completely cleaved from the glycerol substrate (with continual withdrawal of the glycerol from the monoglycerides, diglycerides and triglycerides and the free fatty acids in the vessel 62) and/or by a distillative separation and fractionation of the free fatty acids that sufficiently excludes residual MAG and DAG. Where an optional biodiesel product is desired, a portion of the free fatty acids feed stream 66 is combined with a lower $C_1$-$C_5$ alcohol in a conventional manner and using a known esterification catalyst for making the biodiesel product 68.

The remainder of the free fatty acids feed stream 66 is esterified with one or more alcohols including a five to seven member ring structure, in the presence of an acid esterification catalyst, for example, tin (II) chloride, under conditions which are effective for carrying out the reaction. To drive the reaction to substantial completion, preferably, water is continuously removed as it is formed in the esterification process. Excess alcohol is removed after neutralization by washing and stripping steps, to provide ultimately a very pure unsaturated fatty acid ester product 70, which can in turn be epoxidized in an epoxidation step 72 as previously described to provide the epoxidized unsaturated fatty acid ester plasticizers 74 of the present invention.

These plasticizers 74 again demonstrate improved, and in many cases unexpected, performance attributes as primary plasticizers in polyvinyl halide compositions in which these are used, as illustrated more particularly by the following, non-limiting examples:

EXAMPLE 1

Preparation of Benzyl Soyate Using Sodium Methoxide Catalyst Soy methyl esters (B100 soy biodiesel, Archer Daniels Midland, Mexico, Mo.) were dried of residual moisture with heat and vacuum. Equal weights of soy methyl esters and anhydrous benzyl alcohol (Sigma-Aldrich, St. Louis, Mo.) were placed in a round bottom flask along with a small amount of sodium methoxide catalyst. The mixture was stirred in the flask which was temperature controlled and under strong vacuum. Starting at room temperature, methanol vapor by-product was removed from the flask and recovered in a vacuum cold trap. The reaction temperature was slowly raised to 45-50 degrees C. over a period of 15 hours. Progress of the reaction was monitored by taking periodic samples and checking for residual methyl esters by NMR analysis. The reaction was terminated when less than 2 mole percent methyl esters remained. The mixture was then cooled and subsequently neutralized with citric acid in water. The mixture was then repeatedly washed with 50/50 ethanol/deionized water solutions in reparatory funnels. The washed and separated benzyl ester product was then dried over anhydrous magnesium sulfate, then stripped of any residual benzyl alcohol and water by rotary evaporation. This process provided low color unsaturated fatty acid benzyl esters. Additional decolorizing treatments such as carbon treatment can also be performed to reduce the color.

EXAMPLE 2

Preparation of benzyl soyate from soy free fatty acids Benzyl alcohol (50.73 g) was combined with free fatty acids from soy (128.67 g, S-210, P&G Chemicals, Cincinnati, Ohio), tin(II) chloride (4.35 g Sigma-Aldrich), and toluene (100 mL) in a 500 mL RB flask immersed in a heating oil bath and equipped with a Barrett trap. Under a nitrogen atmosphere, the reagents were brought to reflux (oil bath ~160° C.). The amount of water generated in the reaction was monitored in the Barrett trap; a stoichiometric amount of water, indicating a complete reaction, was 8.3 mL of water. Water collected within the first hour of reflux was disregarded as being impurities in the reactants and reagents. After water collection indicated that the reaction was complete, the reaction mixture was cooled, diluted with ethyl acetate, and transferred to a separatory funnel. The organic layer was washed with the following washes in sequence: water; methanol:water containing 0.1N NaOH (90:10) (twice); methanol:water (90:10); methanol:water (50:50); and water. The organic layer was then dried over magnesium sulfate and ethyl acetate was removed with a rotary evaporator. Toluene was removed under vacuum (1 torr) at 50° C. with stirring until no bubbling was observed.

EXAMPLE 3

Preparation of benzyl soyate using potassium t-butoxide catalyst Soy methyl esters were reacted with anhydrous benzyl alcohol substantially as in Example 1 except potassium t-butoxide (4.2 g, Fluka Chemicals, Sigma-Aldrich) was used as catalyst. The mixture was then cooled to room temperature and then neutralized with citric acid in water. The reaction mixture was cooled and repeatedly washed with ethanol/deionized water solutions in a separatory funnel, then washed with deionized water. Water was removed from the washed benzyl ester product with anhydrous magnesium sulfate. Magnesium sulfate was removed by filtration and the benzyl soyate filtrate was stripped of any residual volatile compounds on a rotary evaporator. NMR analysis on the final washed and stripped product revealed a very pure benzyl soyate containing the following trace impurities (in weight percent): free fatty acids, 0.21%; monoacylglycerols, 0.04%; diacylglycerols, 0.02%, and triacylglycerols, 0.03%.

EXAMPLE 4

Preparation of benzyl soyate using a N-heterocyclic carbene catalyst In a prophetic example, soy methyl esters (100 g) under an inert atmosphere are heated to 90° C. under vacuum to dry and cooled under vacuum. Anhydrous benzyl alcohol (100 g), then a N-heterocyclic carbene (1,3-Bis(2,6-diisopropylphenyl)-1,3-dihydro-2H-imidazol-2-ylidene, Sigma-Aldrich, 100 mg) are added. The mixture is slowly heated to 40° C. over a period of 5 hours while stirring, and reaction progress is monitored by the collection of liberated methanol in a dry-ice trap. The reaction is completed when NMR analysis confirms that methyl esters are no longer present. The reaction is quenched by addition of citric acid solution. The aqueous phase is removed and the reaction mixture is washed 3 times with deionized water. The mixture is dried with anhydrous magnesium sulfate. Any residual benzyl alcohol and water are removed under vacuum.

It can be assumed that benzyl soyate can be synthesized by other established methods for the synthesis of esters such as condensation or transesterification reactions either catalyzed, or mediated by dehydrating agents.

EXAMPLE 5

Preparation of benzyl esters of palm olein using sodium methoxide catalyst In a prophetic example, benzyl esters of palm olein (Archer Daniels Midland, Quincy, Ill.) are prepared substantially as in Example 1.

EXAMPLE 6

Preparation of benzyl esters from palm olein free fatty acids In a prophetic example, benzyl esters of palm olein fatty acids are prepared substantially as in Example 2.

EXAMPLE 7

Preparation of benzyl esters of palm olein using potassium t-butoxide catalyst Palm olein fatty acid methyl esters were prepared at reflux in a round-bottom flask from RBD Palm Olein (ADM Quincy, Ill. facility), anhydrous methanol, and sodium methoxide as catalyst. After completion of the reaction, the product was neutralized with citric acid solution and washed repeatedly with DI water in a separatory funnel. The washed methyl esters were "dried" over anhydrous magnesium sulfate. Magnesium sulfate was filtered out and the filtrate was stripped of residual volatiles on a rotary evaporator to yield the palm olein methyl esters.

About 1050 g of the dry palm olein methyl esters were then reacted with 1200 g anhydrous benzyl alcohol substantially as in Example 1 except potassium t-butoxide (7.0 g, Fluka Chemicals, Sigma-Aldrich) was used as catalyst. After the reaction, the mixture was then cooled to room temperature and then neutralized with citric acid in water. The reaction mixture was repeatedly washed with ethanol/deionized water solutions in a separatory funnel, then washed with deionized water until essentially all residual benzyl alcohol had been removed. Residual moisture was removed from the washed benzyl ester product with anhydrous magnesium sulfate. Magnesium sulfate was removed by filtration and the benzyl palm olein ester filtrate was stripped of any residual volatile compounds on a rotary evaporator. NMR analysis on the final washed and stripped product revealed a very pure benzyl palm olein esters.

EXAMPLE 8

Preparation of benzyl esters of palm olein using a N-heterocyclic carbene catalyst In a prophetic example, benzyl esters of palm olein are synthesized using a N-heterocyclic carbene catalyst substantially as in Example 4.

EXAMPLE 9

Preparation of benzyl esters of linseed oil using sodium methoxide catalyst In a prophetic example, benzyl esters of linseed oil (Archer Daniels Midland, Red Wing, Minn.) are prepared substantially as in Example 1.

EXAMPLE 10

Preparation of benzyl esters from linseed oil free fatty acids In a prophetic example, benzyl esters of linseed oil fatty acids are prepared substantially as in Example 2.

EXAMPLE 11

Preparation of benzyl esters of linseed oil using potassium t-butoxide catalyst Linseed oil fatty acid methyl esters were prepared at reflux in a round-bottom flask at from Superb Linseed Oil (ADM Redwing, Minn. facility), anhydrous methanol, and sodium methoxide as catalyst. After completion of the reaction, the product was neutralized with citric acid solution and washed repeatedly with DI water in a separatory funnel. The washed methyl esters were "dried" over anhydrous magnesium sulfate. Magnesium sulfate was filtered out and the filtrate was stripped of residual volatiles on a rotary evaporator to yield the linseed oil methyl esters.

About 1050 g of the dry linseed fatty acid methyl esters were then reacted with 1200 g anhydrous benzyl alcohol substantially as in Example 1 except potassium t-butoxide (7.0 g, Fluka Chemicals, Sigma-Aldrich) was used as catalyst. After the reaction, the mixture was then cooled to room temperature and then neutralized with citric acid in water. The reaction mixture was repeatedly washed with ethanol/deionized water solutions in a separatory funnel, then washed with deionized water until essentially all residual benzyl alcohol had been removed. Residual moisture was removed from the washed benzyl ester product with anhydrous magnesium sulfate. Magnesium sulfate was removed by filtration and the benzyl linseed fatty acid ester filtrate was stripped of any residual volatile compounds on a rotary evaporator. NMR analysis on the final washed and stripped product revealed a very pure benzyl linseed oil fatty acid esters.

EXAMPLE 12

Preparation of benzyl esters of linseed oil using a N-heterocyclic carbene catalyst In a prophetic example, benzyl esters of linseed oil are synthesized using a N-heterocyclic carbene catalyst substantially as in Example 4.

EXAMPLE 13

Epoxidation of benzyl soyate to form epoxidized benzyl soyate (EBS) Benzyl soyates prepared as in Example 1 were first analyzed to determine the content of free fatty acids (FFA), monoacylglycerols (MAG), diacylglycerols (DAG), and triacylglycerols (TAG) (Table 13.1).

TABLE 13.1

Non-benzyl ester components in benzyl soyate lots. Values are in weight percent.

| Sample Id | FFA | MAG | DAG | TAG |
|---|---|---|---|---|
| Benzyl soyate (for EBS-A and EBS-B, see below) | 0.34 | 0.05 | <0.01 | 0.03 |
| Benzyl soyate (for EBS-C) | 0.83 | 0.05 | 0.01 | 0.05 |

In a procedure adapted from a co-pending, commonly-assigned application filed under the Patent Cooperation Treaty and publishing as WO2006/014483, a 3 gallon bucket was filled with ice and kept within reach during the reaction. Hydrogen peroxide (50%, 500 mL, Sigma-Aldrich) and 96% formic acid (56 mL, Sigma-Aldrich) were chilled to between 0 and 10° C. Soy fatty acid benzyl esters prepared substantially as in co-pending United States Published Patent Application US 2007/0181504 as described above (700 grams) were mixed with water (280 mL) and Tween™ 20 nonionic polysorbate surfactant (5.6 grams, Sigma-Aldrich) in a 2 Liter jacketed round bottom flask with a bottom drain, an overhead stirrer, and an immersion thermocouple. A 4 Liter vessel filled with ice was positioned below the vessel, under the drain valve. The jacket temperature was set to 0° C. and the mixture of soy fatty acids benzyl esters, water, and Tween™ 20 were cooled to less than 10° C. The cold formic acid was carefully mixed with the hydrogen peroxide, taking care to make sure the mixture remained below 10° C.

The cold mixture of hydrogen peroxide and formic acid was carefully poured into the reaction flask, taking care to ensure that the temperature of the mixture remained below 10° C. The temperature was monitored via the immersion thermocouple. If the temperature began to climb rapidly, ice would be added directly to the reaction mixture. If added ice was insufficient to slow the temperature rise and it appeared that the reaction exotherm was out of control, the contents of the flask would have been drained through the drain valve onto the ice container below the vessel. The atmosphere in the flask was made inert with a slow nitrogen purge and the mixture was stirred at 300 rpm. After 1 hour of stirring at 10° C. the jacket temperature was raised to 10° C. and the jacket temperature was raised at a rate of 5° C. every hour until the jacket temperature reached 30° C. At no time was the temperature of the reaction mixture permitted to exceed the jacket temperature by more than 5° C.

When the reaction temperature reached 30° C., reaction progress was monitored by 1H NMR. A 2 mL sample of the reaction mixture was removed by pipette and placed in a centrifuge tube. Hexane (1 mL) was added to the tube and the contents were mixed and allowed to separate. The (lower) aqueous layer was removed by pipette and the remaining layer was washed 3 times with water (2 mL). The hexane was removed by vacuum and the residual oily material was analyzed by 1H NMR. Completion of the reaction was indicated by the disappearance of olefinic proton peaks at 5.3-5.5 ppm and the appearance of oxirane proton peaks at 2.8-3.2 ppm.

Once greater than 99% conversion was achieved, the contents of the flask were transferred to a 4 L separatory funnel and 500 mL of hexanes were added. The contents were mixed and allowed to separate. The aqueous layer was removed and the organic layer was washed with a solution of sodium bisulfite (10%) solution followed by washing with a solution of sodium bicarbonate wash. The sodium bicarbonate wash was removed and the hexanes layer was washed three times with water until the pH of the wash water after washing was 6-8.

Hexanes were removed by vacuum on a rotary evaporator. The conversion to (greater than 95% epoxidation) product was verified by 1H NMR. Three lots of epoxidized benzyl soyate were prepared for testing: Lot 49090140A, labeled EBS-A, Lot 490901408, labeled EBS-B, and Lot 51250051, labeled EBS-C.

The lots were tested by industry standard tests, such as: the hydroxyl values of the lots were determined according to AOCS Tx 1a-66; the acid values were determined according to AOCS method Te 2a-64; the oxirane oxygen values were determined according to AOCS method Cd 9-57; the iodine values were determined according to AOCS method Cd 1-25; and the PtCo Hazen color was determined according to ASTM D1209 (Table 13.2).

TABLE 13.2

Purity of epoxidized benzyl soyates

| Lot number | Hydroxyl value (%) | Acid value | Oxirane oxygen (%) | Iodine value | Color (PtCo Hazen) |
|---|---|---|---|---|---|
| EBS-A | 0.29 | 0.68 | 5.27 | 0.50 | 94 |
| EBS-B | 0.29 | 0.71 | 5.22 | 0.48 | 100 |
| EBS-C | 5.95 | 1.96 | 5.81 | 0.00 | 270 |

EXAMPLE 14

Pre-treatment of fatty acid methyl esters to produce epoxidized benzyl esters with exceptionally light color Purified soy methyl esters (soy biodiesel, 1000 grams, Archer Daniels Midland, Mexico, Mo.) without added antioxidants were dried under heat and vacuum. The peroxide value (PV) of the soy biodiesel was 2 by AOCS Cd 18-90 and the p-anisidine value (pAV) was 4.1 by AOCS Cd 8-53. Sodium borohydride (6 grams, Sigma-Aldrich) was added and the mixture was stirred at 50° C. under vacuum for about 1 hour, then cooled for several hours and filtered. After treatment, the peroxide value of pre-treated FAME had been reduced to 0 and the para-anisidine value was 0.2.

Benzyl soyate was synthesized from 1000 g soy FAME substantially as in Example 1, except that additional benzyl alcohol and 0.5 g of sodium borohydride were added to the reaction after 6 hours of reaction. The progress of the reaction was monitored by NMR analysis. Reaction ended when less than 2 mole % methyl esters remained. The mixture was cooled, neutralized, washed and purified substantially as in Example 3. The benzyl soyate was subsequently treated with activated carbon powder and filtered again. The color of the benzyl soyate product was slight, with Lovibond color values of 1.5 Red, 28.0 Yellow, 0.0 Blue, & 0.8 Neutral. In subsequent epoxidation reaction of this material, the epoxidized benzyl soyate product had a very light color (87) on the Platinum-Cobalt scale. In a control experiment without borohydride treatment, epoxidized benzyl soyate having Lovibond color values of 4.1R, 70.0Y, 0.0B, 2.1N were obtained. When this control EBS was subsequently epoxidized, a Pt—Co color value of 202 was determined. Thus, borohydride treatment was effective at reducing the color of the epoxidized benzyl soyate by greater than 50%.

EXAMPLE 15

Epoxidation of benzyl esters of palm olein to form epoxidized benzyl palm oleate (EBPO) esters The benzyl palm olein esters prepared as described in Example 7 were epoxidized substantially according to the method described in Example 13, starting with 398.34 grams of the benzyl palm olein esters, 100 mL of deionized water and 2.75 grams of the Tween™ 20 nonionic polysorbate surfactant. The same 96% formic acid (20 mL) and 50% hydrogen peroxide (200 mL) solutions were mixed together in preparation for addition to the benzyl esters/water/surfactant mixture as in Example 13

The reaction mixture initially started solidifying, so the temperature was raised to 15 degrees Celsius to keep the mixture liquid. The temperature on addition of the hydrogen peroxide/formic acid mixture stayed stable, so the temperature of the reaction medium was immediately raised to 40 degrees Celsius. On determining that the reaction had reached completion, the resultant epoxidized benzyl palm olein esters were then washed, worked up and tested as in Example 13. The testing showed an iodine value of 0.64, an oxirane oxygen value of 3.28%, an hydroxyl value of 0.69%, an acid value of 0.415 and a PtCo Hazen color of 84.

EXAMPLE 16

Epoxidation of benzyl esters of linseed oil to form epoxidized benzyl linolate esters The benzyl linseed oil fatty acid esters prepared in Example 11 were also epoxidized substantially as in Example 13, starting with 509.45 grams of the benzyl esters, 100 mL of deionized water and 2.56 grams of Tween™ 20 nonionic polysorbate surfactant. Twenty milliliters of 96% formic acid and 381.33 grams of 50% hydrogen peroxide solution were combined and added slowly to the reaction vessel. Upon completion of the reaction, washing and work up of the resultant epoxidized benzyl linolate esters, the materials were tested for iodine value (5.65), oxirane oxygen (8.4 percent), hydroxyl value (8.84 percent), acid value (0.47) and PtCo Hazen color (198).

Compounding and Evaluation Protocols for Examples 17 and Following:

Compounding of PVC Plastisols The materials listed in Table A were used for compounding a set of PVC plastisols. Two samples (DINP and BBP) were formulated as reference samples using commercial phthalate primary plasticizers, and three samples (EBS-A, EBS-B and EBS-C) were formulated as experimental samples. Results for EBS-A and EBS-B are provided for Examples 17 and 18, respectively, while certain additional test results for EBS-A and the results for EBS-C are provided in Example 19.

TABLE A

Raw Material List (Examples 17-19).

| Material and Mol. Wt. | Brand Name | Generic Name | Source | Source Location |
|---|---|---|---|---|
| Geon 121AR | Geon ™ 121AR | Homopolymer PVC Dispersion Resin | PolyOne, Inc. | Avon Lake, OH |
| DINP 419 Daltons | | Di-isononyl phthalate | | |
| BBP 312 Daltons | Santicizer ™ 160 | Butyl Benzyl Phthalate | Ferro, Inc. | Cleveland, OH |
| EBS-A 383 Daltons | | Epoxidized Benzyl Soyate | ADM (lot 49090140A) | Decatur, IL |
| EBS-B 383 Daltons | | Epoxidized Benzyl Soyate | ADM (lot 49090140B) | Decatur, IL |
| EBS-C 383 Daltons | | Epoxidized Benzyl Soyate | ADM (lot 51250051) | Decatur, IL |
| ESO | Plas-Chek ™ | Epoxidized Soybean Oil | Ferro, Inc. | Cleveland, OH |
| LOHF 120 | Therm-Chek ™ | Ba/Zn stabilizer | Ferro, Inc. | Cleveland, OH |

Plastisol (PVC) Formulation Protocol Materials from Table A were used in compounding plastisols of Example 17-19 in the following quantities: Geon 121AR Resin, 100 parts; plasticizer, 67 parts; epoxidized soybean oil, 3 parts; Ba/Zn stabilizer (LOHF 120), 2 parts. Weighed powdered solids were introduced to a 1-gallon mixing bowl. The primary plasticizer and other liquid components were combined in a separate container. The solids in the mixing bowl were stirred at the lowest speed of a 3-Speed Hobart Paddle Mixer, and the liquids were slowly added to the mixing bowl. The contents were mixed for about 30 minutes, and the mixture was subjected to vacuum (such as in a large dessicator) to reduce air entrapment.

Test Protocols for PVC Plastisol Examples

Where results are reported below for the various plastisol specimens (in Examples 17 and following), the corresponding tests were carried out according to the following protocols:

Paste Viscosity—The paste viscosity of a plastisol specimen describes the flow behavior of plastisols under low shear. The suitability of a dispersion resin for a given application depends on the viscosity characteristics of the plastisol and indicates performance in pouring, casting, molding, and dipping processes. The Paste Viscosity Test (Brookfield Viscosity Test) was carried out substantially according to ASTM procedure D1824 using a Brookfield RVFD Viscometer. Measurements were made at room temperature at 2 revolutions per minute (RPM) and 20 RPM. Low initial paste viscosity is desired for ease of handling, with preferably as little increase as possible over time, so that the paste viscosity measurements were repeated on several occasions over 30 days to determine the stability of the paste viscosity of the plastisol specimens.

Gloss—The gloss test (20 and 60 Degree Gloss Test) was carried out substantially according to ASTM D2457. This is a clear wearlayer test that is often applied as a standard test of plastisols. Gloss is determined at high temperatures (350° F. or 390° F.).

Air Release—The Air Release Test is carried out to determine the relative speed of release of entrained air from a plastisol. Liquid plastisol is poured into at 4 ounce polypropylene cup or equivalent and the plastisol is stirred vigorously with a spatula for one minute. As the entrapped air rises to the surface, the rate at which the bubbles break is observed and recorded. A relative rating of "Excellent" to "Poor" is assigned by comparison with reference formulations. Excellent air release (5 minutes) is obtained with a reference formulation comprising 100 parts Geon™ 121AR, 67 parts DINP, 3 parts epoxidized soybean oil (ESO), and 2 parts Therm-Chek™ LOHF 120. Poor air release (>60 minutes) is obtained with a reference formulation comprising 100 parts Geon™ 121AR, 67 parts BBP, 3 parts ESO, and 2 parts Therm-Chek™ LOHF 120.

Hardness—The Shore A Hardness test is carried out substantially according to ASTM D2240 using a Shore Durometer Gage to determine the hardness values of plastisols. Hardness is a measure of the efficiency of the plasticizer. At equal levels of incorporation of two different plasticizers in otherwise identical plastisols, the plasticizer yielding the softer plastisol is a more efficient plasticizer.

Heat Stability—The Metrastat Heat Stability test is used to measure the thermal stability of a plastisol film at high temperatures. Fused sheets of plastisols are prepared and exposed to high temperatures for varying time periods along the length of the strips. An excellent plastisol does not discolor or char and maintains flexibility after the test. Fused sheets of plastisol are prepared by "drawing down" plastisol onto a heat-stable surface (release substrate) using a 20 mil (0.020") drawing bar; the release substrate must be capable of withstanding at least 200° C. (390° F.) for 5 minutes. The fused sheets ("draw downs") are fused for 3 minutes in an oven at 200° C. (390° F.). Fused sheets are allowed to cool at room temperature for a minimum of 15 minutes before removing from the release substrate. Sample strips measuring 25 cm (9.75 inch) by 2.5 cm (1 inch) are cut from the fused sheets. A Metrastat™ oven is preheated to 191° C. (375° F.) and sample strips are placed onto the travelling tray of the Metrastat™ oven. A one hour exposure cycle is started. As the tray travels the sample strips are exposed to the oven temperature over a time gradient of 0-60 minutes. When the cycle is complete, sample strips are allowed to cool for 1 hour and mounted onto display paper which shows the time the sample was exposed to high heat.

Gelation—The gel curve and gelation temperature test is carried out to determine the viscosity of plastisols under increasing temperature with a CarriMed™ CSL-2 500 rheometer. The gelation temperature indicates the solvating power of the plasticizer; lower gelation temperatures indicate greater solvating power, and are preferred for convenience in applications such as screen printing, dip coating, and preparation of soft rubber compounds because less heat is needed to maintain low viscosity of the plastisols. The viscosity is plotted as a function of temperature, and analysis of the plot indicates an approximate gelation temperature. A 4 centimeter flat, steel spindle is attached to the rotor of the rheometer and the calibration routine is carried out to calibrate the spacing between the rheometer Peltier plate and the spindle. An increase in temperature from 20° C. to 100° C. (68° F. to 212° F.) at a rate of 0.1° C. (0.18° F.) per second with a constant shear rate of 5 sec-1 is programmed into the rheometer software. A 2 gram sample of plastisol is loaded onto the Peltier plate and the program is initiated. At the conclusion of the temperature ramp, the results are plotted as output of viscosity versus temperature on a semi-Log chart to produce a gel curve. Then, lines are hand-drawn asymptotically to the two sections of the gel curve, extending them toward the X axis until they intersect. The gel temperature is then approximated by noting the temperature corresponding to the intersection of the hand-drawn lines.

Tensile and Tear Strength—The Tensile and Tear Strength test is carried out substantially according to ASTM Method D 638 (type 4) using an Instron™ instrument to determine the ability of plastisols to retain elongation after heating and cooling. Plastisol strips are heated to various temperatures (325-400 degrees C.) and cooled and pulled until they fail by tearing or breaking, and the stress at break and strain at break are recorded. Higher stress and strain at break indicate greater retention of properties after heat aging.

Yellowness Index—The Yellowness test was carried out substantially according to ASTM 1925. Fused sheets of plastisol strips were prepared by drawing down plastisol on a Form 2C Leneta opacity chart to a 20 mil thickness of wet plastisol. The wet plastisol was fused by heating at 390° F. for 3 minutes and the strip was cooled at room temperature for at least an hour. Yellowness was measured using a Datacolor International SpectraFlash SF300 spectrophotometer with ColorTools QC ProTools v1.2 software after setting the following parameters in the software Instrument setup: Calibration Mode=Reflectance; Specular Port=Included; Viewing=LAV; and UV Amount=UV Included. Flashes per read were set to "1" and the spectrophotometer was calibrated using the "C 2 Deg" set or parameters. After calibration the "D 1925 Yellowness Index" set or parameters were selected. Measurements were taken by measuring the E313 standard reference material first, then the fused plastisol sample on the white portion of the Leneta opacity chart. The spectrophotometer calculates and displays the yellowness index of the sample relative to the E313 standard Heat Loss—The Heat Loss test is applied to fused plastisols to determine the percent loss of mass during heat aging. Low heat loss is desirable, as volatilized plasticizer can contaminate nearby surfaces, such as windshield interiors on new cars. Fused sheets of plastisol are prepared substantially as in the Heat Stability Test. Square samples (5.0 cm by 5.0 cm (2 inch by 2 inch)) are punched or cut and weighed to +/−0.0001 g. The samples are incubated in an 82° C. (180° F.) oven for 7 and/or 14 days, and cooled for 30 minutes before re-weighing. The heat loss is expressed as a percentage of the original weight of the sample.

Plasticizer Volatility—The Plasticizer Volatility test is used to determine the relative plasticizer volatility that may affect plastisol processing. Lower plasticizer volatility is desired, especially for compounded (extruded) plastisols. A 1-gram sample of plasticizer is accurately weighed (+/−0.0001 g) and incubated in an oven for 3 minutes at 204° C. (400° F.). The weight loss is determined and the percentage of weight loss is reported as plasticizer volatility.

Elongation and Retention of Elongation—The Retention of Elongation Test is used to determine the retention of elongation of fused plastisol samples after heat aging. Less loss of elongation after heat aging is desirable. Fused sheets of plastisol are prepared substantially as in the Heat Stability Test. From the finished sheets, for each plastisol, four (4) sets of five (5) die-cut sample pieces are cut out using an ASTM D 412-68 Type C die. One set of five sample pieces is retained as a control, and the remaining sets of five sample pieces are heat aged by incubating at 191° C. (375° F.) for 20 minutes, 40 minutes, and 60 minutes, respectively. Elongation of each set of die cut samples is determined per ASTM D-638 (type 4) by elongating the samples to a standard length by pulling, and then measuring the amount of the standard length that is retained when the pulling force is removed. The retention of elongation (ROE) is expressed as a percent of the elongation of the heat aged samples relative to the elongation of the control.

Glass Transition Temperature by Quick Plasticization Test—A quick plasticization test is used to determine a glass transition temperature of a plastisol and is a useful quick screening tool. Quick plasticization plastisols were compounded by mixing plasticizer at 10, 25, or 50 percents into PVC (Formosa Plastics, Livingston, N.J.).

The resulting plastisol powders are then compression molded with a stainless steel mold comprising a base plate, a plunger, and a mold cylinder as follows. The mold cylinder comprised a height of 22.5 mm, an outer diameter of 76 mm, and a cylindrical chamber having an internal diameter of 11 mm. The outer diameter of the plunger was 10.975 mm. The base plate comprised an outer ring and a raised inner plunger of 10.975 mm. Two discs of aluminum foil having a diameter of 10.975 mm are prepared. The base plate is fitted to the mold and an aluminum disc is placed onto the top surface of the base plate. PVC plastisol is weighed into an aluminum dish, stirred, and heated in a 120° C. oven for one minute before placing 0.8 grams into the mold atop the aluminum disc. The mold is tamped to remove voids and a second disc of aluminum foil is placed atop the PVC material in the mold. The cylinder is fitted to the mold and pressed in by hand as far as possible. The filled mold is placed into a press having the jack plates preheated to 160° C. The lower plate is raised until the clamping force reaches 4000 psi. The press heaters are then turned off and the clamping force is maintained at 4000 psi by hand as cooling air is applied to the jack. The jack plate temperature is cooled to 40° C. and the sample is removed from the mold.

To determine a glass transition temperature, a TA Instruments (New Castle, Del.) Q400 Thermomechanical Analyzer was equipped with a macroexpansion probe and samples were placed under a force of 0.005N and heated from −80 deg C. to 80 deg C. The dimension change was recorded and the glass transition temperature was found by plotting the intersection of the trendlines of the linear regions above and below the glass transition temperature.

Exudation Test—Fused plastisol discs are made in aluminum weighing dishes using from 15+/−0.5 grams of liquid plastisol. Three discs per plastisol sample are prepared. The plastisols are fused for ten minutes in an oven preheated to 400° F. The discs are cooled quickly in water and removed from the aluminum dishes. To determine exudation, a stack of two fused plastisol discs is incubated in a 180° F. oven for at least 4 weeks. The discs are examined after 24 hours and weekly for at least four weeks and compared with an identical reference strip kept at room temperature. The visible presence of exudation is noted, and the amount exuded is determined by visual inspection. Exudation values are assigned as falling into one of the following ranges: trace-light-moderate-heavy.

EXAMPLE 17

Testing epoxidized benzyl soyate plastisols made from EBS-A

Paste Viscosity results of plastisols made from EBS-A are presented in Table 17.1.

TABLE 17.1

Paste viscosity of two reference plastisol formulations using commercial phthalate primary plasticizers and a plastisol formulation using inventive epoxidized benzyl soyate EBS-A. (Units are in cPs (centiPoise) and were obtained with spindle 3 except where noted with an asterisk.)

|  | DINP | BBP | EBS-A |
|---|---|---|---|
| 20 rpm |  |  |  |
| Initial | 3,230 | 4,800 | 2,085 |
| 1 Day | 3,435 | 4,045 | 2,205 |
| 3 Day | 3,625 | 4,495 | 2,485 |
| 7 Day | 3,680 | 4,685 | 2,540 |
| 14 Day | 4,080 | 5,000* | 2,785 |
| 30 Day | 3,700 | 5,550* | 3,350 |
| 2 rpm |  |  |  |
| Initial | 2,300 | 2,600 | 1,550 |
| 1 Day | 2,650 | 2,400 | 1,650 |
| 3 Day | 2,750 | 2,500 | 1,900 |
| 7 Day | 2,750 | 2,950 | 1,900 |
| 14 Day | 3,000 | 2,500* | 2,050 |
| 30 Day | 3,000 | 3,100* | 2,600 |

*Spindle 4

Each plastisol showed a slight increase in viscosity over time. Plastisols made with the inventive EBS plasticizer had desirable lower initial paste viscosities, and desirable stable paste viscosities over time. Consequently the viscosity performance of plastisols made with EBS plasticizer was better than the viscosity performance and stability of plastisols made with DINP or BBP.

Gloss—Values at 20 degrees and 60 degrees were determined and are presented in Table 17.2.

TABLE 17.2

Gloss values (%) of plastisols made with EBS and controls.

| Sample | DINP | BBP | EBS-A |
|---|---|---|---|
| 20° Gloss 3"@390° F. | 82.1 | 86.4 | 85.4 |
| 20° Gloss 5"@350° F. | 29.1 | 39.9 | 42.0 |
| 60° Gloss 3"@390° F. | 90.0 | 95.5 | 92.2 |
| 60° Gloss 5"@350° F. | 71.1 | 85.8 | 82.0 |

The epoxidized benzyl soyate imparted excellent comparable gloss characteristics to the plastisols. Gloss values of the plastisol made with epoxidized benzyl soyates were comparable to the gloss values of the plastisol made with BBP and somewhat higher than gloss values of plastisol made with DINP.

The Air Release of plastisol made with epoxidized benzyl soyate was compared to the air release of plastisols made with DINP and BBP (Table 17.3).

TABLE 17.3

Air release (minutes) of plastisols made with EBS and controls.

| Sample | DINP | BBP | EBS-A |
|---|---|---|---|
| Air Release minutes) | 5 | >60 | 45 |

Plastisol made with EBS showed a useable air release time, better than a plastisol made with BBP.

Hardness: The Shore A Hardness of plastisol made with epoxidized benzyl soyate was compared to the hardness of plastisols made with DINP and BBP (Table 17.4).

TABLE 17.4

Hardness values of plastisols made with EBS and controls.

| Sample | DINP | BBP | EBS-A |
|---|---|---|---|
| Hardness | 84 | 77 | 76 |
| Hardness (repeat) | 85 | 79 | 77 |

The hardness value of the plastisol made with EBS was very good, comparable to plastisols made with BBP. Both plastisols made with BBP and EBS-A were slightly lower in hardness than the plastisol made with DINP. Thus, EBS is a strong solvating, highly efficient primary plasticizer like BBP.

The Metrastat Heat Stability of plastisol made with epoxidized benzyl soyates as the primary plasticizer was compared to the Metrastat Heat Stability of plastisols made with DINP and BBP as primary plasticizers (FIG. 4) and revealed improved and unexpected characteristics in plastisols made with epoxidized benzyl soyate. The Metrastat Heat stability of plastisol made with EBS-A was excellent, and far excelled that of the controls. Control samples darkened and charred, whereas the fused plastisol strip made with EBS-A remained free from any visible charring. In addition, manual inspection of the sample strips revealed that both control fused plastisol strips were hard and brittle, whereas the fused plastisol strip made with EBS-A remained soft, supple, and pliable.

Gelation: The gel curves and gelation temperatures indicate that the inventive EBS primary plasticizers are highly solvating and fast fusing. The EBS-A plastisol and BBP plastisol both showed an onset of gelation temperature of 60 degrees, while DINP required a higher temperature for onset of gelation (fusion).

The Tensile and Tear Strength of a plastisol made with EBS-A was compared to the tensile strength of plastisols made with DINP and BBP at temperatures ranging from 325° F. to 400° F. (Tables 17.5a and 17.5b).

TABLE 17.5a

Stress at break (psi) of plastisols made with EBS-A and controls.

| Temperature | DINP | BBP | EBS-A |
|---|---|---|---|
| 325° F. | 741 | 1750 | 1,230 |
| 350° F. | 1,380 | 2,140 | 2,000 |
| 375° F. | 2,040 | 2,410 | 1,950 |
| 400° F. | 2,370 | 2,200 | 1,940 |

TABLE 17.5b

Strain at break (%) of plastisols made with EBS-A and controls.

| Temperature | DINP | BBP | EBS-A |
|---|---|---|---|
| 325° F. | 65 | 314 | 221 |
| 350° F. | 174 | 404 | 424 |
| 375° F. | 376 | 433 | 447 |
| 400° F. | 473 | 399 | 452 |

The stress at break values and strain at break values of the EBS-A plastisol were similar to values obtained with plastisols made from DINP and BBP.

The Yellowness Index of a plastisol made with an epoxidized benzyl soyate of the present invention was determined substantially according to ASTM 1925 and compared to the Yellowness Index of plastisols made with DINP and BBP and to the E313 standard sometimes used for flooring (Table 17.6).

TABLE 17.6

Yellowness index of plastisols made with EBS and controls compared with the E313 standard

| Sample | DINP | BBP | EBS-A |
|---|---|---|---|
| Yellow Index ASTMD 1925 | 19.73 | 21.18 | 24.97 |
| Yellow Index E313 Std. | 16.77 | 18.13 | 21.15 |

Plastisols made with control primary plasticizers DINP and BBP exhibited better Yellowness Index values, but the plastisol made with EBS was within acceptable ranges.

The Heat Loss of plastisol made with the inventive epoxidized benzyl soyate was compared to the heat loss of plastisols made with DINP and BBP (Table 17.7).

TABLE 17.7

Percent heat loss of plastisols made with EBS and controls at 180° F. at day 7 and day 18.

| Sample | DINP | BBP | EBS-A |
|---|---|---|---|
| 7 Days | 0.7% | 5.1% | 1.5% |
| 18 Days | 1.2% | 10.6% | 2.0% |

The plastisol made with EBS showed excellent heat loss values at 7 and 18 days. The low heat loss illustrates improved and unexpected characteristics because the molecular weight of EBS primary plasticizers is much lower than the molecular weight of the control primary plasticizers.

EXAMPLE 18

Testing epoxidized benzyl soyate plastisols made from EBS-B Plastisols made from EBS B were tested to compare with commercial plasticizers and EBS-A. Reference data for DINP and BBP are reproduced from Example 17.

Paste Viscosity results of plastisols made from EBS-B are presented in Table 18.1.

TABLE 18.1

Paste viscosity of two reference plastisol formulations using commercial phthalate primary plasticizers and a plastisol formulation using inventive epoxidized benzyl soyate.
(Units are in cPs (centiPoise) and were obtained with spindle 3 except where noted with an asterisk.)

| | DINP | BBP | EBS-B |
|---|---|---|---|
| 20 rpm | | | |
| Initial | 3,230 | 4,800 | 2,340 |
| 1 Day | 3,435 | 4,045 | 2,435 |
| 3 Day | 3,625 | 4,495 | 2,725 |
| 7 Day | 3,680 | 4,685 | 2,745 |
| 14 Day | 4,080 | 5,000* | 3,085 |
| 30 Day | 3,700 | 5,550* | 3,455 |
| 2 rpm | | | |
| Initial | 2,300 | 2,600 | 1,850 |
| 1 Day | 2,650 | 2,400 | 1,900 |
| 3 Day | 2,750 | 2,500 | 2,400 |
| 7 Day | 2,750 | 2,950 | 2,150 |
| 14 Day | 3,000 | 2,500* | 2,250 |
| 30 Day | 3,000 | 3,100* | 2,650 |

*Spindle 4

Each plastisol showed a slight increase in viscosity over time. Plastisol made with the inventive EBS plasticizer had desirable lower initial paste viscosities, and desirable stable paste viscosities over time. Consequently the viscosity performance of plastisol made with EBS-B plasticizer was better than the viscosity performance and stability of plastisols made with DINP or BBP.

Gloss—Values at 20 degrees and 60 degrees were determined and are presented in Table 18.2.

TABLE 18.2

Gloss values (%) of plastisols made with EBS-B and controls.

| Sample | DINP | BBP | EBS-B |
|---|---|---|---|
| 20° Gloss 3"@390° F. | 82.1 | 86.4 | 85.7 |
| 20° Gloss 5"@350° F. | 29.1 | 39.9 | 41.4 |
| 60° Gloss 3"@390° F. | 90.0 | 95.5 | 92.2 |
| 60° Gloss 5"@350° F. | 71.1 | 85.8 | 81.7 |

The epoxidized benzyl soyate imparted excellent comparable gloss characteristics to the plastisol. Gloss values of the plastisol made with epoxidized benzyl soyate were comparable to the gloss values of the plastisol made with BBP and somewhat higher than gloss values of plastisol made with DINP.

The Air Release of plastisol made with epoxidized benzyl soyate was compared to the air release of plastisols made with DINP and BBP (Table 18.3).

TABLE 18.3

Air release (minutes) of plastisols made with EBS and controls.

| Sample | DINP | BBP | EBS-B |
|---|---|---|---|
| Air Release minutes) | 5 | >60 | 45 |

Plastisol made with EBS-B showed a useable air release time, better than plastisol made with BBP.

Hardness: The Shore A Hardness of plastisol made with epoxidized benzyl soyate was compared to the hardness of plastisols made with DINP and BBP (Table 18.4).

TABLE 18.4

Hardness values of plastisols made with EBS-B and controls.

| Sample | DINP | BBP | EBS-B |
|---|---|---|---|
| Hardness | 84 | 77 | 75 |

The hardness value of plastisol made with EBS-B was very good, comparable to plastisols made with BBP. Both EBS-B plastisol and BBP plastisol were slightly lower in hardness than the plastisol made with DINP. Thus, EBS is a strong solvating, highly efficient primary plasticizer like BBP.

The Metrastat Heat Stability of plastisol made with epoxidized benzyl soyate as the primary plasticizer was compared to the Metrastat Heat Stability of plastisols made with DINP and BBP as primary plasticizers (FIG. 4) and revealed improved and unexpected characteristics in plastisols made with epoxidized benzyl soyate. The Metrastat Heat stability of plastisol made with EBS-B was excellent, and far excelled that of the controls. Control samples darkened and charred, whereas the fused plastisol strip made with EBS B remained free from any visible charring. In addition, manual inspection of the sample strips revealed that both control fused plastisol strips were hard and brittle, whereas the fused plastisol strip made with EBS-B remained soft, supple, and pliable.

Gelation: The gel curves and gelation temperatures indicate that the inventive EBS primary plasticizers are highly solvating and fast fusing. The EBS-B samples and BBP all showed an onset of gelation temperature of 60 degrees, while DINP required a higher temperature for onset of gelation (fusion).

The Yellowness Index of plastisol made with epoxidized benzyl soyates was determined substantially according to ASTM 1925 and compared to the Yellow Index of plastisols made with DINP and BBP and to the E313 standard sometimes used for flooring (Table 18.5).

TABLE 18.5

Yellow index of plastisol made with EBS-B and controls compared with the E313 standard

| Sample | DINP | BBP | EBS-B |
|---|---|---|---|
| Yellow Index ASTMD 1925 | 19.73 | 21.18 | 25.08 |
| Yellow Index E313 Std. | 16.77 | 18.13 | 21.24 |

Plastisols made with control primary plasticizers DINP and BBP exhibited better Yellowness Index values, but the plastisol made with EBS-B was within acceptable ranges.

The Heat Loss of plastisol made with epoxidized benzyl soyates was compared to the heat loss of plastisols made with DINP and BBP (Table 18.6).

TABLE 18.6

Percent heat loss of plastisols made with EBS-B and controls at 180° F. at day 7 and day 18.

| Sample | DINP | BBP | EBS-B |
|---|---|---|---|
| 7 Days | 0.7% | 5.1% | 1.1% |
| 18 Days | 1.2% | 10.6% | 1.9% |

The plastisol made with EBS-B showed excellent heat loss values at 7 and 18 days. The low heat loss illustrates improved and unexpected characteristics because the molecular weight of EBS primary plasticizers is much lower than the molecular weight of the control primary plasticizers.

The Glass Transition Temperature of plastisols made with several contents of an inventive epoxidized benzyl soyate were tested. EBS-A was incorporated into plastisols at 10%, 25%, and 50% levels. Results are presented in Table 18.7

TABLE 18.7

Glass transition temperatures of plastisols made with EBS-A by the quick plasticization test.

| EBS-A content | Glass transition temperature (° C.) |
|---|---|
| 10% | 63.46 |
| 25% | 39.90 |
| 50% | −1.90 |

EXAMPLE 19

Plastisols were prepared from the materials listed in Tables 19.1 substantially as outlined for example 17.

TABLE 19.1

Experimental Raw Material List

| Material | Brand Name | Generic Name | Commercial Source | Source Location |
|---|---|---|---|---|
| Geon 121AR | Geon ™ 121AR | Homopolymer PVC Dispersion Resin | PolyOne Inc. | Avon Lake, OH |
| EBS-A | | Epoxidized Benzyl Soyate | ADM | Decatur, IL |
| EBS-C | | Epoxidized Benzyl Soyate | ADM | Decatur, IL |
| BBP | Santicizer ™ 160 | Butyl Benzyl Phthalate | Ferro, Inc. | Cleveland, OH |
| Mesamoll II plasticizer | Mesamoll ™ II | Alkylsulfonic acid phenylester | Lanxess Inc. (USA) | Pittsburg, PA |

TABLE 19.1-continued

Experimental Raw Material List

| Material | Brand Name | Generic Name | Commercial Source | Source Location |
|---|---|---|---|---|
| Jayflex 77 plasticizer | Jayflex ™ 77 | DIHP, Diisoheptyl Phthalate | ExxonMobil, Inc. | Houston, TX |
| ESO | Plas-Chek ™ | Epoxidized Soybean Oil | Ferro, Inc. | Cleveland, OH |
| LOHF 120 | Therm-Chek ™ | Ba/Zn stabilizer | Ferro, Inc. | Cleveland, OH |

Lot EBS-A was used for all of the tests in this Example, except for the Elongation/Retention of Elongation test, in which Lot EBS-C was used. The testing protocols were as described above, with the results below:

|  | EBS-A | BBP | Mesamoll II | Jayflex 77 |
|---|---|---|---|---|
| Brookfield Paste Viscosity at 20 RPM | | | | |
| 20 rpm | | | | |
| Initial | 1,600 | 3,675 | 4,820 | 1,990 |
| 1 Day | 1,600 | 3,400 | 4,660 | 1,960 |
| 4 Day | 1,915 | 4,000 | 5,160 | 2,250 |
| 7 Day | 1980 | 4060 | 5150 | 2250 |
| 14 Day | 2,225 | 4,325 | 5,090 | 2,410 |
| 21 Day | 2,365 | 4,375 | 5,190 | 2,575 |
| 29 Day | 2,485 | 4,925 | 5,290 | 2,625 |
| Brookfield Paste Viscosity at 2 RPM | | | | |
| 2 rpm | | | | |
| Initial | 1,050 | 2,300 | 3,000 | 1,500 |
| 1 Day | 1,000 | 2,050 | 2,800 | 1,400 |
| 4 Day | 1,150 | 2,650 | 3,000 | 1,600 |
| 7 Day | 1250 | 2400 | 3000 | 1600 |
| 14 Day | 1,300 | 2,400 | 2,500 | 1,650 |
| 21 Day | 1,300 | 3,000 | 3,600 | 1,650 |
| 29 Day | 2,150 | 3,400 | 4,000 | 2,400 |
| Air Release (minutes) | | | | |
| Air Release | Poor | Poor | Poor | Excellent |
| Hardness (Shore A) | | | | |
| Hardness | 77 | 79 | 80 | 80 |
| Plasticizer Volatility (% loss) | | | | |
| Volatility | 6.43% | 3.83% | 6.06% | 1.55% |
| Yellowness Index (ASTM D1925) on Leneta | | | | |
| Yellowness Index | 25.67 | 21.67 | 21.35 | 20.45 |
| Heat Loss @ 180° F. (%) | | | | |
| 6 Days | 1.6% | 10.4% | 2.0% | 8.0% |
| 14 Days | 2.5% | 16.4% | 3.4% | 14.8% |
| Tensile: Stress at break (psi) | | | | |
| 325° F. | 1,230 | 1,750 | 1,550 | 1,110 |
| 350° F. | 2,000 | 2,140 | 2060 | 1,750 |
| 375° F. | 1,950 | 2,410 | 2030 | 2,090 |
| 400° F. | 1,940 | 2,200 | 2230 | 2,130 |
| Strain at break (%) | | | | |
| 325° F. | 221 | 314 | 226 | 182 |
| 350° F. | 424 | 404 | 369 | 336 |
| 375° F. | 447 | 433 | 381 | 439 |
| 400° F. | 452 | 399 | 418 | 437 |

| | EBS-C | | BBP | | Mesamoll II | | Jayflex 77 | |
|---|---|---|---|---|---|---|---|---|
| | Elongation | ROE | Elongation | ROE | Elongation | ROE | Elongation | ROE |
| Elongation and Retention of Elongation (ROE) (%) | | | | | | | | |
| 0 min | 406 | 100 | 357 | 100 | 347 | 100 | 419 | 100 |
| 20 min | 407 | 100 | 266 | 75 | 363 | 105 | 295 | 70 |
| 40 min | 332 | 82 | 206 | 58 | 273 | 79 | 145 | 35 |
| 60 min | 299 | 74 | 102 | 29 | 246 | 71 | 138 | 33 |

As in Examples 17 and 18, each plastisol showed a slight increase in viscosity over time. The plastisol made with the inventive EBS-A plasticizer had a lower initial paste viscosity, and a desirably stable paste viscosity. Consequently the viscosity performance of the EBS-A plastisol was better than the viscosity performance and stability of the plastisols made with the commercial primary plasticizers BBP, Mesamoll II and Jayflex 77.

The Shore A hardness of the EBS-A plastisol was very low, as in Example 17 and 18. The Yellowness index value was similar to that obtained in Example 17 and 18. The plasticizer volatility of the EBS-A plastisol was relatively high compared to BBP and Jayflex 77, yet the plastisol made from EBS-A had unexpectedly excellent (low) heat loss at both 6 days and 14 days, with lower heat loss than Mesamoll II plastisol and much lower heat loss than BBP plastisol and Jayflex 77 plastisol. The stress at break and strain at break values of the EBS-A plastisol were comparable to the control plastisols.

The elongation and retention of elongation performance of the plastisol made with EBS-C as a primary plasticizer was better overall than the performances of plastisols made with the commercial products BBP, Mesamoll II and Jayflex 77. The elongation of the EBS-C plastisol was approximately that of the Jayflex 77 plastisol, but the EBS-C plastisol retained its elasticity and pliability to a much greater extent than the Jayflex 77 plastisol and on par, generally, with the Mesamoll II plastisol.

EXAMPLE 20

Preparation and epoxidation of tetrahydrofurfuryl alcohol monosoyate from soy free fatty acids. Tetrahydrofurfuryl alcohol (40.22 grams, PennAKem, Memphis, Tenn.), an alcohol with a five-membered ring, was filtered and combined with free fatty acids from soy (109.48 grams, ADM, Decatur, Ill.), tin(II) chloride (3.7718 grams, Aldrich), and toluene (100 mL, Aldrich) substantially as outlined in example 2. A stoichiometric amount of water (7 mL), indicating a complete reaction, was removed. The reaction mixture was cooled, diluted with ethyl acetate, and washed, then ethyl acetate and toluene were removed, substantially as outlined in example 2. About 100 mL of an orange-yellow liquid tetrahydrofurfuryl alcohol soyate product with a brown tint was obtained.

Tetrahydrofurfuryl alcohol soyate (61.49 grams) was epoxidized substantially as outlined in example 13. Nonionic polysorbate surfactant (Tween™ 20, 0.49 grams, Sigma-Aldrich), formic acid (4.919 grams, Sigma-Aldrich) hydrogen peroxide (43.9214 grams, Fisher), and water (24.595 ml) were used. After addition of hexanes, washes, and evaporation, 53.24 grams of a light pale yellow clear liquid (epoxidized tetrahydrofurfuryl alcohol soyate) were obtained.

Quick plasticization test Epoxidized tetrahydrofurfuryl alcohol soyate (ETHFS) was mixed with PVC for the quick plasticization test at 10%, 25%, and 50% levels to determine the effect of the ETHFS on glass transition temperatures. A TA Instruments (New Castle, Del.) Q400 Thermomechanical Analyzer was equipped with a macroexpansion probe and samples were placed under a force of 0.005N and heated from −80 deg C. to 80 deg C. The dimension change was recorded and the glass transition temperature was found by using the intersection of the trendlines of the linear regions above and below the glass transition temperature. Results are presented in Table 20.1

TABLE 20.1

Glass transition temperatures of plastisols made with ETHFS by the quick plasticization test.

| ETHFS content | Glass transition temperature (° C.) |
|---|---|
| 10% | 65.43 |
| 25% | 44.27 |
| 50% | −20.09 |

Two lots of ETHFS were prepared substantially as described above to obtain ETHFS samples with widely varying hydroxyl values. ETHFS lot 51250073 (ETHFS73), having a hydroxyl value of 21.2, and ETHFS lot 51250074 (ETFHS74) having a hydroxyl value of 145, were incorporated into plastisols. and compared to control plastisols made with plasticizers comprising one of EBS64-lot 51250064, Jayflex 77, or Mesamoll II. The intrinsic volatility of these various plasticizers is given in table 20.2, the formulations of the plastisols are given in Table 20.3, and test results are given in Table 20.4

TABLE 20.2

Intrinsic plasticizer volatility (%).

| | 15-B EBS | 15-C Jayflex | 15-D Mesamoll | 15-E ETHFS73 | 15-F ETHFS74 |
|---|---|---|---|---|---|
| Volatility (% loss) | 6.5 | 1.6 | 5.9 | 2.8 | 2.8 |

TABLE 20.3

Composition of plastisols made with epoxidized esters of five-membered ring alcohols (ETHFS) and controls. Values are in parts. ESO is epoxidized soybean oil.

| | 15-B EBS | 15-C Jayflex | 15-D Mesamoll | 15-E ETHFS73 | 15-F ETHFS74 |
|---|---|---|---|---|---|
| 121AR Resin | 100 | 100 | 100 | 100 | 100 |
| EBS lot 51250064 | 70 | 0 | 0 | 0 | 0 |
| Jayflex 77 | 0 | 67 | 0 | 0 | 0 |
| Mesamoll II | 0 | 0 | 67 | 0 | 0 |
| ETHFS 51250073 | 0 | 0 | 0 | 70 | 0 |
| ETHFS 51250074 | 0 | 0 | 0 | 0 | 70 |
| ESO | 0 | 3 | 3 | 0 | 0 |
| LOHF 120 | 2 | 2 | 2 | 2 | 2 |

TABLE 20.4

Characteristics of plastisols made with epoxidized esters of five-membered ring alcohols (ETHFS) and control plasticizers. For exudation results, trace exudation means that exudation was observed only on the outer edge of fused discs. Light exudation means that exudation was present only on the outer edge enclosing the top outer surface.

| Sample name → | 15-B EBS | 15-C Jayflex | 15-D Mesamoll | 15-E ETHFS73 | 15-F ETHFS74 |
|---|---|---|---|---|---|
| Air release | Poor | Excellent | Poor | Poor | Poor |
| Shore A Hardness | 77 | 79 | 83 | 73 | 73 |
| Gelation temp. ° C. | 58 | 66 | 66 | 54 | 55 |
| Heat Loss (%) 1 week @180° F. | 1.5% | 4.9% | 1.4% | 1.4% | 1.4% |
| Heat Loss (%) 2 weeks @180° F. | 1.9% | 8.1% | 2.1% | 2.0% | 1.9% |
| Brookfield Paste Viscosity (cPs) 20 rpm | | | | | |
| Initial/spindle 3 | 1,140 | 1,480 | 3,455 | 2,505 | 4,930 |
| 1 Day (spindle#/result) | 3/1,520 | 3/1,865 | 4/4,380 | 3/4,400 | 4/8,950 |
| 2 Day (spindle#/result) | 3/1,655 | 3/1,965 | 4/4,720 | 4/5,740 | 5/12,840 |
| 5 Day (spindle#/result) | 3/2,045 | 3/2,385 | 4/5,690 | 5/9,060 | 5/18,920 |
| 7 Day/ (spindle#/result) | 3/2,105 | 3/2,465 | 4/5,690 | 5/11,360 | 6/19,750 |
| 14 Day (spindle#/result) | 3/2,265 | 3/2,555 | 4/5,850 | 6/17,350 | 6/29,250 |
| 21 Day (spindle#/result) | 3/2,410 | 3/2,575 | 4/5,600 | 6/26,050 | 6/41,650 |
| 28 Day (spindle#/result) | 3/2,880 | 4/2,815 | 4/5,630 | 6/39,900 | 7/63,200 |
| 2 rpm | | | | | |
| Initial/spindle 3 | 1,000 | 1,250 | 3,150 | 2,300 | 5,700 |
| 1 Day (spindle#/result) | 3/1,350 | 3/1,650 | 4/3,300 | 3/4,550 | 4/11,500 |
| 2 Day (spindle#/result) | 3/1,500 | 3/1,750 | 4/3,700 | 4/6,000 | 5/17,800 |
| 5 Day (spindle#/result) | 3/1,900 | 3/2,100 | 4/4,200 | 5/10,000 | 5/27,800 |
| 7 Day/ (spindle#/result) | 3/1,950 | 3/2,300 | 4/4,300 | 5/12,600 | 6/29,500 |
| 14 Day (spindle#/result) | 3/2,150 | 3/2,450 | 4/4,700 | 6/21,500 | 6/48,000 |
| 21 Day (spindle#/result) | 3/2,300 | 3/2,550 | 4/4,700 | 6/35,000 | 6/68,500 |
| 28 Day (spindle#/result) | 3/2,950 | 3/2,650 | 4/4,900 | 6/62,500 | 7/134,000 |

TABLE 20.4-continued

Characteristics of plastisols made with epoxidized esters of five-membered ring alcohols (ETHFS) and control plasticizers. For exudation results, trace exudation means that exudation was observed only on the outer edge of fused discs. Light exudation means that exudation was present only on the outer edge enclosing the top outer surface.

| Sample name → | 15-B EBS | 15-C Jayflex | 15-D Mesamoll | 15-E ETHFS73 | 15-F ETHFS74 |
|---|---|---|---|---|---|
| Exudation at room temperature | | | | | |
| 24 hours | None | None | None | None | None |
| 7 days | None | None | None | None | None |
| 14 days | None | None | None | None | None |
| 21 days | None | None | None | None | None |
| 28 days | None | None | None | None | None |
| 35 days | None | None | None | None | None |
| Exudation at 180° F. | | | | | |
| 24 hours | None | None | None | None | None |
| 7 days | None | None | None | None | None |
| 14 days | None | None | None | None | None |
| 21 days | None | None | None | Trace | Trace |
| 28 days | None | None | None | Light | Light |
| 35 days | None | None | None | Light | Moderate |

In addition, samples were subjected to the Metrastat heat stability test. Fused plastisol strips made with Jayflex 77 and Mesamoll II once again darkened and charred, whereas the fused plastisol strips made with EBS and ETHFS remained free from any visible charring. In addition, manual inspection of the sample strips revealed that both control fused plastisol strips were hard and brittle after the Metrastat heat test. The fused plastisol strip made with ETHFS73 took about 60 minutes to turn a very pale yellow and did not blacken at all. The fused plastisol strip made with ETHFS73 also remained soft, supple, and pliable, with flexibility similar to the EBS fused plastisol strips tested in Example 17 and 18.

EXAMPLES 21 AND 22

A high purity, epoxidized benzyl soyate primary plasticizer product was prepared as Example 21 in the manner of Example 3, by reacting 500 grams of reFlex 100™ epoxidized methyl soyate esters (from PolyOne Corporation, Avon Lake, Ohio USA) with 600 grams of anhydrous benzyl alcohol, in the presence of 4 grams of potassium t-butoxide as a catalyst. The epoxidized methyl soyate esters were of a high purity in keeping with the present invention, being made as described herein. The epoxidized methyl soyate esters and benzyl alcohol were transesterified over approximately 11 hours at between 35 to 40 degrees Celsius under vacuum, to produce a high purity epoxidized benzyl soyate product for evaluation while removing the methanol byproduct. Completion of the reaction was verified by NMR spectroscopy. After neutralizing the catalyst with added 50% citric acid solution, the EBS product was washed multiple times with deionized water in a separatory funnel, including some ethyl ether with the deionized water to facilitate the washing. The washed product was dried of moisture with anhydrous magnesium sulfate. After filtration to remove the magnesium sulfate, residual ethyl ether materials were stripped from the product by rotary evaporation, and excess benzyl alcohol was removed in a lab-scale molecular still at 90 degrees Celsius and 0.29 millibars.

The second alternative process for making high purity EBS was demonstrated for comparison by reacting 350 grams of reFlex 100™ epoxidized methyl soyate esters (from PolyOne Corporation, Avon Lake, Ohio USA) with 400 grams of anhydrous benzyl acetate in the presence of 8 grams of sodium methoxide powder and 3 grams of a 30% sodium methoxide solution in methanol. This interesterification process was carried out over about 7 hours at 30 degrees Celsius under vacuum, to produce an epoxidized benzyl soyate product for evaluation while removing methyl acetate as a byproduct. Completion of the reaction was verified by NMR spectroscopy. After neutralizing the catalyst with added 50% citric acid solution, the EBS product was washed multiple times with deionized water in a separatory funnel, including some ethyl ether with the deionized water to facilitate the washing. The washed product was dried of moisture with anhydrous magnesium sulfate. After filtration to remove the magnesium sulfate, residual ethyl ether materials were stripped from the product by rotary evaporation, and excess benzyl acetate was removed in a lab-scale molecular still at 90 degrees Celsius and 0.30 millibars.

The EBS products so made were then formulated into plastisols in PVC as described above for the other examples 17 et seq., with 70 phr of EBS and 2.00 phr of Ba/Zn thermal stabilizer LOHF 120™ (Ferro Inc., Cleveland, Ohio USA), and the plastisols evaluated in turn by means of the tests outlined and described above.

Results were as shown below in Table 21.1, against a plastisol made with a commercial Jayflex 77™ diisoheptyl phthalate plasticizer:

TABLE 21.1

Plastisols Made from EBS Derived from EMS by Transesterification and by Interesterification

| Sample name → | Jayflex 77 | EBS (Ex. 21 - Alcohol) | EBS (Ex. 22 - Acetate) |
|---|---|---|---|
| Air release | Excellent | Poor | Poor |
| Shore A Hardness | 76 | 75 | 72 |
| Gelation temp. ° C. | 67 | 63 | 59 |
| Heat Loss (%) 1 week @180° F. | 5.6 | 0.9 | 3.6 |
| Heat Loss (%) 2 weeks @180° F. | 9.6 | 1.2 | 4.7 |
| Brookfield Paste Viscosity (cPs) 20 rpm | | | |
| Initial/spindle 3 | 1925 | 1380 | 1115 |
| 1 Day | 2190 | 1675 | 1330 |
| 3 Day | 2445 | 1685 | 1565 |
| 7 Day | 2450 | 1985 | 2035 |
| 14 Day | 2595 | 2220 | 2435 |
| 21 Day | 2715 | 2490 | 2675 |
| 28 Day | 2800 | 2635 | 3045 |
| 2 rpm | | | |
| Initial/spindle 3 | 2050 | 1250 | 950 |
| 1 Day | 2250 | 1600 | 1100 |
| 3 Day | 2500 | 1600 | 1300 |
| 7 Day | 2500 | 1750 | 1800 |
| 14 Day | 2650 | 2150 | 2400 |
| 21 Day | 2750 | 2200 | 2850 |
| 28 Day | 2900 | 2450 | 3000 |
| Exudation at room temperature | | | |
| 24 hours | None | None | None |
| 7 days | None | None | None |
| 14 days | None | None | None |
| 21 days | None | None | None |
| 28 days | None | None | None |
| 35 days | None | None | None |

TABLE 21.1-continued

Plastisols Made from EBS Derived from EMS by Transesterification and by Interesterification

| Sample name → | Jayflex 77 | EBS (Ex. 21 - Alcohol) | EBS (Ex. 22 - Acetate) |
|---|---|---|---|
| Exudation at 180° F. | | | |
| 24 hours | None | None | None |
| 7 days | None | None | None |
| 14 days | None | None | None |
| 21 days | None | None | None |
| 28 days | None | None | None |
| 35 days | None | None | None |

The plastisols were also evaluated for their heat loss values in comparison to the plastisol made with the commercial phthalate plasticizer. After 7 days at 180 degrees Fahrenheit, the plastisol using the phthalate plasticizer exhibited a mass loss of 5.6%, while the EBS-based plastisols showed mass losses of 0.9% and 3.6% for the benzyl alcohol and benzyl acetate preparations, respectively. After 14 days, the commercial phthalate-based plastisol showed a mass loss of 9.6%, as compared to 1.2% and 4.7% only from the two EBS-based plastisols.

Finally, specimens prepared and tested by means of the Metrastat heat stability test verified that the EBS-based materials behaved in the same manner when prepared starting from the epoxidized methyl soyates (epoxidized biodiesel materials) as when starting from methyl soyates (unepoxidized biodiesel materials), with much improved heat stability as compared to a specimen prepared using the Jayflex 77™ phthalate plasticizer.

What is claimed is:

1. A polyvinyl halide composition comprising a polyvinyl halide polymer and an epoxidized soyate ester composition of the combined epoxidized esters of the fatty acids in soybean oil, in which the ester moiety is characterized by a five to seven member ring structure, which epoxidized soyate ester composition contains not more than about 5.0 percent by weight of monoglycerides and diglycerides combined.

2. A polyvinyl halide composition according to claim 1, wherein the epoxidized soyate ester composition contains not more than about 2.0 percent by weight of monoglycerides and diglycerides.

3. A polyvinyl halide composition according to claim 2, wherein the epoxidized soyate ester composition contains not more than about 0.4 percent by weight of monoglycerides and diglycerides.

4. A polyvinyl halide composition according to claim 3, wherein the epoxidized soyate ester composition contains not more than about 0.25 percent by weight of monoglycerides and diglycerides.

5. A polyvinyl halide composition according to claim 1, wherein the epoxidized soyate ester composition predominantly comprises the epoxidized benzyl esters of the fatty acids in soybean oil.

6. A polyvinyl halide composition according to any of claims 1, 2, 3, 4 or 5, wherein the epoxidized soyate ester composition is used as a primary plasticizer component.

7. A polyvinyl halide composition according to claim 6, wherein the epoxidized soyate ester composition is not less than about 20 percent by weight of the polyvinyl halide composition.

8. A polyvinyl halide composition according to claim 7, wherein the epoxidized soyate ester composition is from about 20 to about 50 percent by weight of the polyvinyl halide composition.

9. A polyvinyl halide composition according to claim 8, wherein the epoxidized soyate ester composition is from about 30 to about 50 percent by weight of the polyvinyl halide composition.

10. A polyvinyl halide composition according to claim 8, wherein the epoxidized soyate ester composition is from about 40 to about 50 percent by weight of the polyvinyl halide composition.

11. A polyvinyl halide composition according to claim 10, further comprising an epoxidized vegetable oil as a secondary plasticizer.

12. A polyvinyl halide composition according to claim 11, which is plasticized only by the epoxidized soyate ester composition as a primary plasticizer and an epoxidized vegetable oil secondary plasticizer.

* * * * *